(12) United States Patent
Webb et al.

(10) Patent No.: US 10,671,704 B2
(45) Date of Patent: Jun. 2, 2020

(54) PREDICTING IMMUNE RESPONSE

(71) Applicant: PrioBio, LLC, Concord, CA (US)

(72) Inventors: Timothy Webb, Concord, CA (US);
Jesse Cotari, San Francisco, CA (US);
Justin Rebo, Crockett, CA (US);
Stuart Alexander Jacobson, San Francisco, CA (US)

(73) Assignee: PRIOBIO, LLC, Concord, CA (US)

( * ) Notice: Subject to any disclaimer, the term of this patent is extended or adjusted under 35 U.S.C. 154(b) by 490 days.

(21) Appl. No.: 15/215,465

(22) Filed: Jul. 20, 2016

(65) Prior Publication Data

US 2017/0024536 A1    Jan. 26, 2017

Related U.S. Application Data

(60) Provisional application No. 62/195,837, filed on Jul. 23, 2015.

(51) Int. Cl.
*G06F 19/00* (2018.01)
*G09B 7/02* (2006.01)
(Continued)

(52) U.S. Cl.
CPC ........ *G06F 19/3418* (2013.01); *A61B 5/0022* (2013.01); *A61B 5/021* (2013.01); *A61B 5/024* (2013.01); *A61B 5/02055* (2013.01); *A61B 5/0531* (2013.01); *A61B 5/1113* (2013.01); *A61B 5/1118* (2013.01); *A61B 5/14542* (2013.01); *A61B 5/15* (2013.01); *A61B 5/150022* (2013.01); *A61B 5/150305* (2013.01); *A61B 5/150343* (2013.01); *A61B 5/150351* (2013.01); *A61B 5/41* (2013.01);
(Continued)

(58) Field of Classification Search
CPC .......... G09B 7/00; G06F 19/3418; A61B 5/15
See application file for complete search history.

(56) References Cited

U.S. PATENT DOCUMENTS 6,416,471 B1    7/2002 Kumar et al.
2002/0146672 A1    10/2002 Burdea et al.
(Continued)

FOREIGN PATENT DOCUMENTS

WO    2010/071915 A1    7/2010
WO    2012/042437 A2    4/2012
(Continued)

OTHER PUBLICATIONS

International Search Report and Written Opinion from related International Application No. PCT/US2016/043425, dated Oct. 6, 2016; 9 pgs.
(Continued)

*Primary Examiner* — Jason Skaarup
(74) *Attorney, Agent, or Firm* — Polsinelli PC; Tara A. Nealey

(57) ABSTRACT

Systems, methods, and non-transitory computer-readable storage media for gathering activity data describing a user's activities from one or more activity sensors and using the activity data to predict immune-response to the activity. Predicting immune-response can involve creating, personalizing, and refining immune-response prediction models based on demographic user data, activity data, blood sample data, personal genetic information.

9 Claims, 21 Drawing Sheets

(51) Int. Cl.

| | | |
|---|---|---|
| *A61B 5/15* | (2006.01) | |
| *A61B 5/11* | (2006.01) | |
| *A61B 5/00* | (2006.01) | |
| *A61B 5/021* | (2006.01) | |
| *A61B 5/024* | (2006.01) | |
| *A61B 5/145* | (2006.01) | |
| *A61B 5/0205* | (2006.01) | |
| *A61B 5/053* | (2006.01) | |
| *G09B 5/12* | (2006.01) | |
| *A61B 5/151* | (2006.01) | |

(52) U.S. Cl.
CPC ............ *A61B 5/486* (2013.01); *A61B 5/7275* (2013.01); *A61B 5/7475* (2013.01); *G09B 5/125* (2013.01); *G09B 7/02* (2013.01); *A61B 5/150099* (2013.01); *A61B 5/15105* (2013.01); *A61B 5/15113* (2013.01); *A61B 5/15117* (2013.01); *A61B 5/15142* (2013.01); *A61B 5/150251* (2013.01); *A61B 5/150412* (2013.01); *A61B 5/150755* (2013.01); *A61B 5/7264* (2013.01); *A61B 2503/10* (2013.01); *A61B 2505/09* (2013.01)

(56) References Cited

U.S. PATENT DOCUMENTS

| | | |
|---|---|---|
| 2004/0122706 A1 | 6/2004 | Walker et al. |
| 2009/0198516 A1 | 8/2009 | Greenholtz |
| 2009/0271219 A1 | 10/2009 | Hyde et al. |
| 2010/0241465 A1* | 9/2010 | Amigo .................. G06Q 40/08 705/4 |
| 2011/0212090 A1 | 9/2011 | Pedersen et al. |
| 2011/0285529 A1 | 11/2011 | Pendse |
| 2012/0035509 A1 | 2/2012 | Wilson et al. |
| 2014/0066884 A1 | 3/2014 | Keenan et al. |
| 2015/0184222 A1 | 7/2015 | Yeh |
| 2016/0016041 A1* | 1/2016 | Giedwoyn ......... A63B 24/0021 700/91 |
| 2016/0078471 A1* | 3/2016 | Hamedi .................. H04L 67/02 705/14.41 |
| 2016/0210839 A1* | 7/2016 | Yadav ................ G08B 21/0492 |

FOREIGN PATENT DOCUMENTS

| | | |
|---|---|---|
| WO | 2014/086803 A1 | 6/2014 |
| WO | 2015/054701 A2 | 4/2015 |
| WO | 2017/015509 A1 | 1/2017 |
| WO | 2017/015589 A1 | 1/2017 |

OTHER PUBLICATIONS

International Search Report and Written Opinion from International Application No. PCT/US2016/043641, dated Dec. 8, 2016; 11 pgs.
Bocher et al., "Kinetics of Hepatitis B Surface Antigen-Specific Immune Responses in Acute and Chronic Hepatitis B or After HBs Vaccination: Stimulation of the In Vitro Antibody Response by Interferon Gamma," Hepatology, 1999, pp. 238-244, vol. 29, No. 1.
Extended European Search Report from European Patent Application No. 16828572.4, dated Feb. 20, 2019; 9 pgs.
Partial European Search Report from European Patent Application No. 16828629.2, dated Apr. 2, 2019; 13 pgs.

* cited by examiner

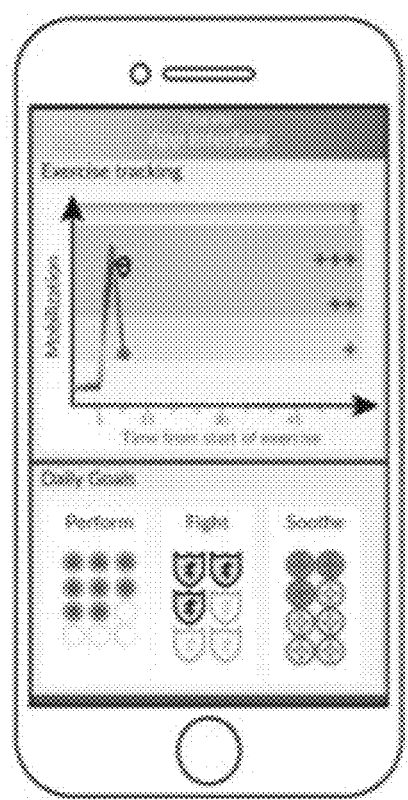
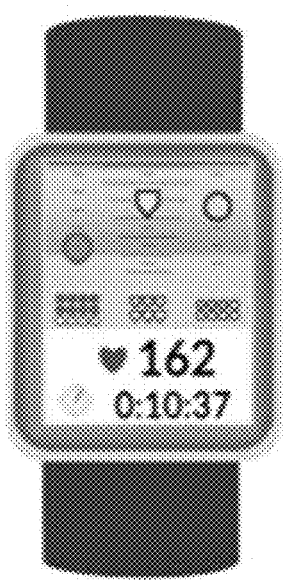
FIG. 2D                    FIG. 2E

PREDICTING IMMUNE RESPONSE

CROSS REFERENCE TO RELATED APPLICATIONS

This application claims priority to U.S. provisional application No. 62/195,837, filed on Jul. 23, 2015, entitled "METHOD AND SYSTEM FOR CELL MOBILIZATION", which is expressly incorporated by reference herein in its entirety.

TECHNICAL FIELD

The present technology pertains to immunotherapy, and more specifically pertains to optimizing blood cell mobilization.

BACKGROUND

Blood cells, such as stem cells, blood progenitors, red blood cells and all major types of white blood cells, can be effectively mobilized by exercise. Therefore, exercise can affect immunity in a variety of ways. For example, regular, moderate-intensity exercise can help protect people against some diseases, particularly those that involve the upper respiratory track (like colds). However, too much exercise can have the opposite effect and reduce immunity. There is a need in the art for notifying a person about how much exercise is enough, when exercise is appropriate and when it's not, which types of exercise are appropriate for their particular situation, and other exercise-immunity related information. There is also a need in the art for personalizing an immune-affecting activity recommendation based on a person's intrinsic characteristics as well as quantified variable personal traits.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and non-transitory computer-readable storage media for creating, personalizing, and refining immune-response prediction models based on demographic user data, activity data, blood sample data, personal genetic information.

Some embodiments of the present technology involve a user device that can be used to enter user information and create, based on the user information, a recommended baseline activity regimen for achieving at least one immunity-related goal. The recommended baseline activity regimen for achieving at least one immunity-related goal can be created using an immune-response prediction model stored in the memory or obtained from a network location. The user device can also be coupled with an activity sensor and can receive activity data for the user from the activity sensor. The activity sensor can be physically integrated into the user device or can be wirelessly coupled with the user device. The user device can also be simultaneously coupled with a plurality of activity sensors that collect a variety of user activity data. The activity sensors can be one or more of a heart rate monitor, an accelerometer, a blood pressure monitor, an external temperature monitor, a body temperature monitor, a location tracking system, a pressure sensor, a skin conductance sensor, a blood oxygen level sensor blood sugar monitor, pace maker, etc.

The user device can determine when the activity data indicates a user activity that deviates from the recommended baseline activity regimen and can provide feedback on the user device for correcting the deviation from the recommended baseline activity regimen. The user device can display, as part of the recommended baseline activity regimen, one or more of an activity type, an exertion intensity and an exertion duration.

Some embodiments of the present technology also involve the user device displaying interface elements selectable on the user device to op-in to allowing the user device to retrieve the user's blood sample data and/or personal genetic information and to update the recommended baseline activity regimen based on the blood sample data and/or personal genetic information. The user device can also personalize the recommended baseline activity regimen based on the blood sample data and/or personal genetic information to create an updated activity regimen that increases the mobilization of one or more specific blood cells.

Some embodiments of the present technology also involve method of providing feedback to user devices relating to how activity predictively affects immune-response. The present technology can involve methods for receiving self-reported user input data relating to immune-response, creating a recommended baseline activity regimen based on the self-reported user input data. The recommended baseline activity regimen can be created by using a clinically created blood mobilization model and inputting the user information into the blood mobilization model.

Some embodiments of the present technology also involve receiving, from an activity sensor, activity data for the user, determining that the activity data indicates an activity that deviates from the recommended baseline activity regimen to a predetermined threshold degree, and providing feedback on the user device regarding the deviation from the recommended baseline activity regimen.

Further the present technology can involve methods including receiving user consent to retrieve personal medical information, blood sample data, personal genetic information, etc. and using the collected information to personalizing the recommended baseline activity regimen Some embodiments of the present technology also involve methods of priming a blood donor by mobilizing certain therapeutic blood cells. The methods can involve entering self-reported information for a user into a clinically created blood mobilization model and creating a recommended baseline activity regimen for increasing the mobilization of one or more therapeutic blood cell. Also, priming a blood donor can involve receiving activity data from an activity sensor worn by the user, determining when the user activity deviates from the recommended baseline activity regimen to a predetermined threshold degree, and providing feedback on the user device for correcting the deviation from the recommended baseline activity regimen.

Some embodiments of the present technology also involve methods, apparatus, and computer-readable medium that can display a predicted blood mobilization response. These embodiments can involve inputting user information into a clinically-created immune-response model for a statistical population to create a personalized immune-response model, identifying, based on the personalized immune-response model, an activity that is predicted to produce a blood mobilization response for the user, and displaying the activity and the predicted blood mobilization response. These embodiments can also involve receiving activity data from the user and modifying the user interface element based on a predicted effect that the received activity data is predicted to have on the predicted blood mobilization response. Also, blood sample data can be used to determine a correlation between the user activity and an actual blood mobilization response observed in the blood sample data and the correlation can be used to modify the personalized immune-response model and to determine an activity modification that will predictively increase the blood mobilization response of the activity for the user. Likewise, blood sample data can also be used to confirm predicted correlations between the user activity and cell surface proteins of immune cells.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIGS. 2A-2E illustrate examples of graphical user interfaces for displaying immune-response information according to some embodiments of the present technology;

DESCRIPTION

Figure 1:
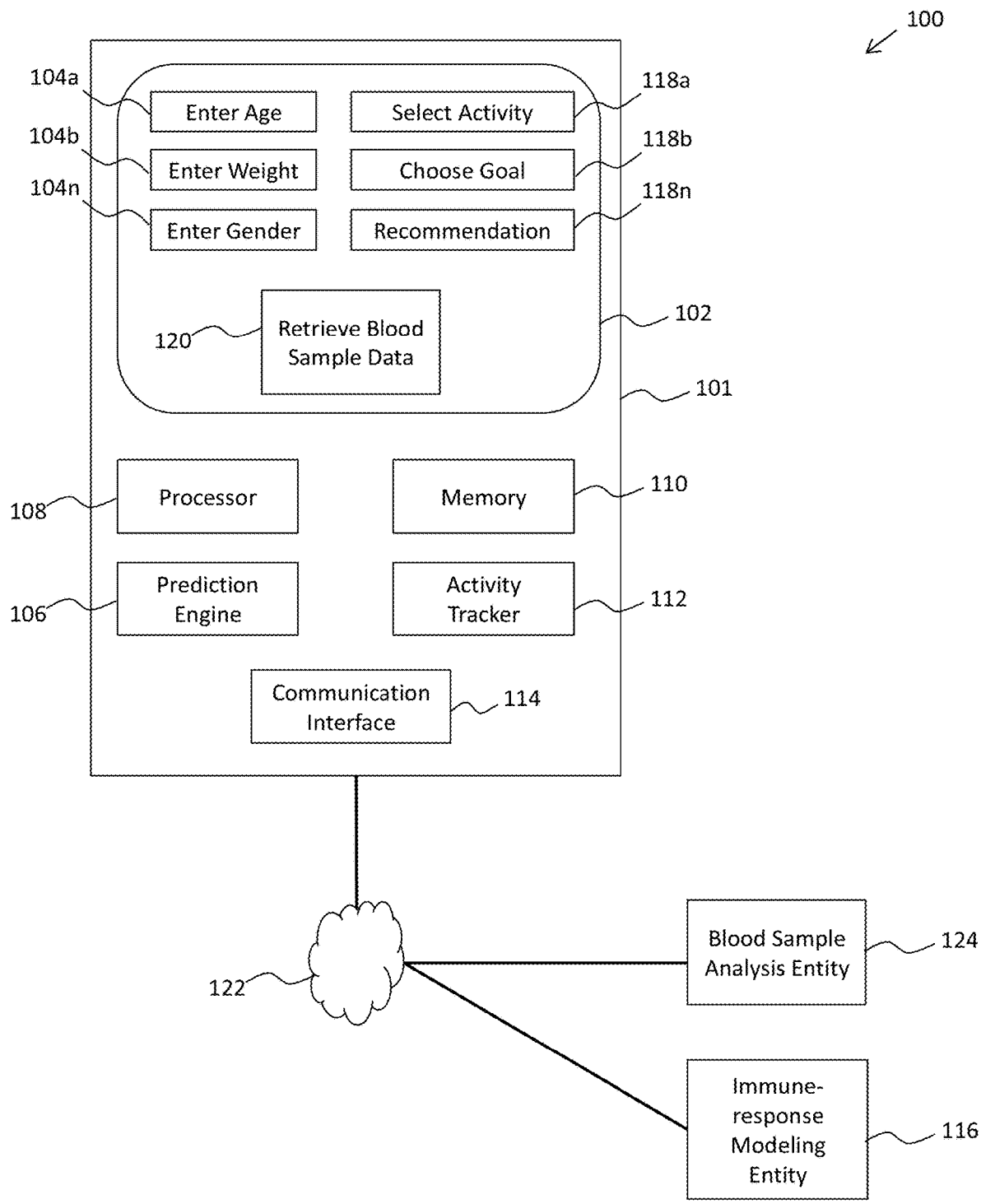
FIG. 1 illustrates a system for displaying how activity can affect their immune health according to some embodiments of the present technology.
Figure 2A:
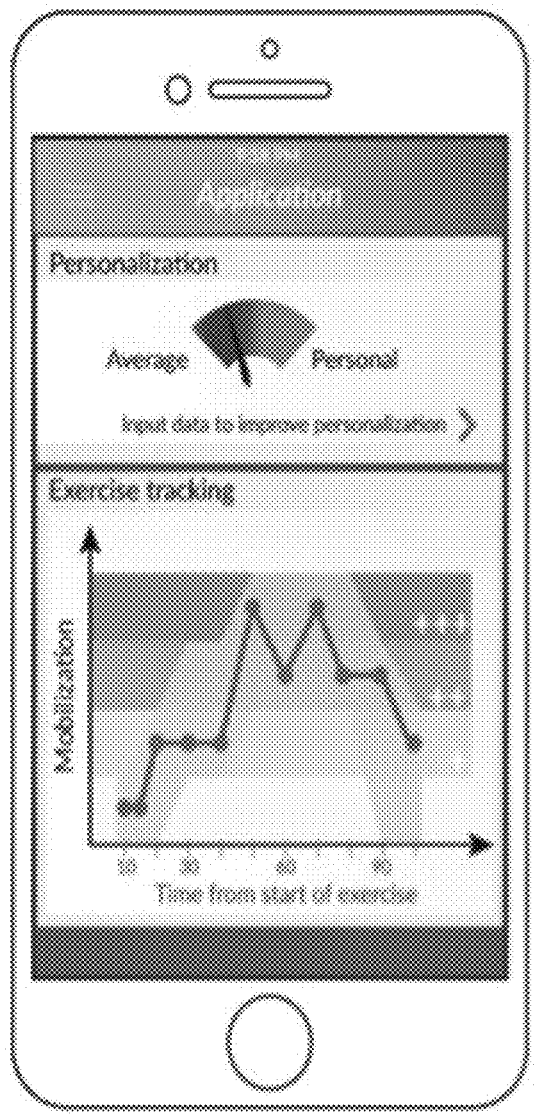
Figure 2B:
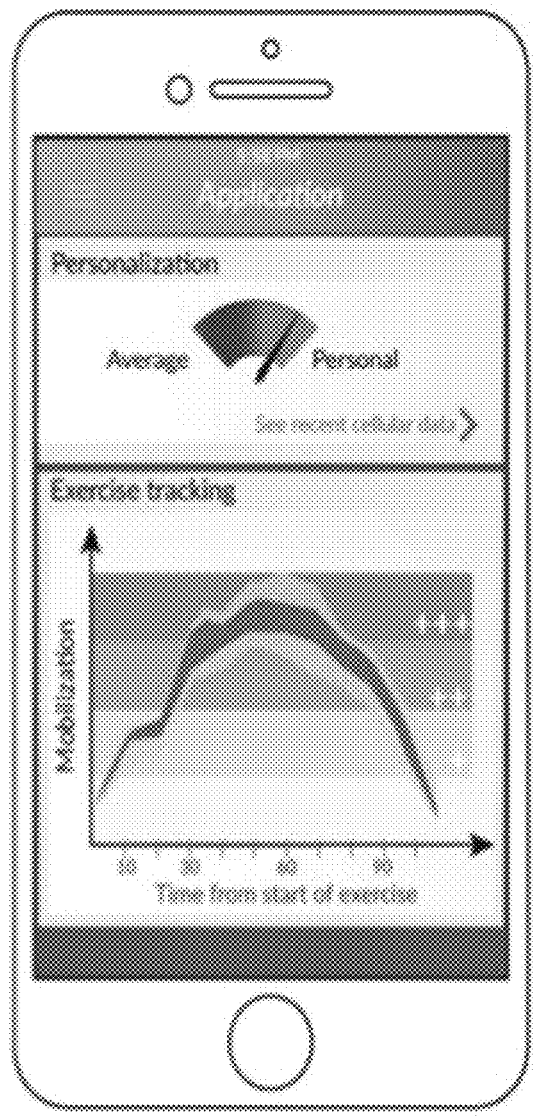
Figure 2C:
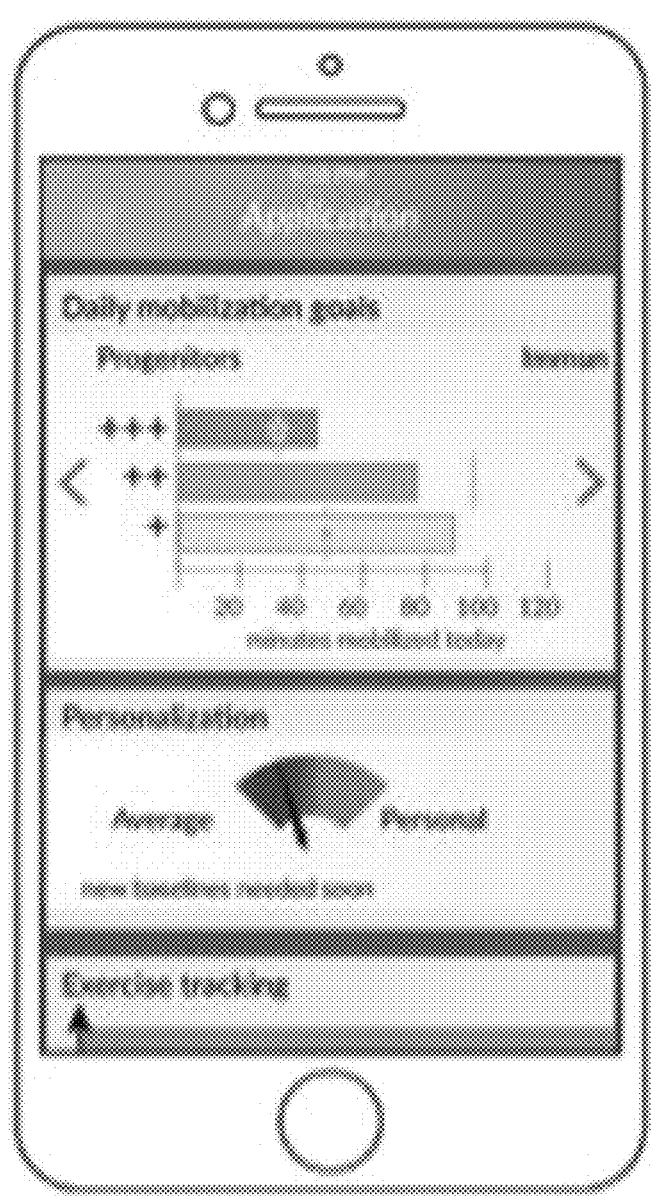

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

The disclosed technology addresses the need in the art for personalizing an immune-response model based on a person's intrinsic characteristics and based on quantified variable personal traits. The disclosed technology also addresses the need for predicting how users' activities will affect an immune-response and personalizing an immune-response model based on blood sample data post activity. The disclosed technology also addresses the need for notifying users about how their activities will predictively affect an immune-response. For example, notifying a user can include notifying the user how much exercise is enough to achieve an immunity-related goal, when exercise is appropriate to achieve the immunity-related goal, when exercise can be detrimental to an immunity-related goal, which types of exercise are appropriate for their particular situation to achieve the immunity-related goal, and other activity-related immunity information.

As explained above, blood cells, such as stem cells, blood progenitors, red blood cells and all major types of white blood cells, can be effectively mobilized through human activity. Some embodiments of the present technology involve controlling the circulation of mature immune cells and immune progenitor cells through real-time correlation to baseline health and exercise metrics such as heart rate. In some situations, controlling circulation, changes in immune cell proteins and surface structure, etc. can be achieved by using brief, moderate to high intensity aerobic exercise. For example, in some cases exercise times do not have to exceed five minutes to achieve some mobilization. Also, in some cases, longer exercise can cause the concentration of white blood cells and stem/progenitors to decline more rapidly following an initial increase in concentration. Also, circulating immune system changes occur from almost any activity including light walking or even standing.

Some embodiments of the present technology involve creating immune-response prediction models by observing mobilization following exercise and quantifying the effects using clinical analysis, e.g. cytometric assays Immune-response is significantly affected by blood cell mobilization; therefore, the present disclosure sometimes refers specifically to predicting changes to mobilization, personalizing mobilization models, determining correlations between activities and mobilization, mobilization goals, etc. However, those with ordinary skill in the art having the benefit of the present disclosure will readily understand that the present technology can be applied to predicting changes to other immune-response factors, personalizing other immune-response models based on other immune-response factors, determining correlations between activities and other immune-response factors, other immune-response goals, modulation of circulatory or tissue levels of cells, changes in surface proteins on an immune cell, etc.

The immune-response prediction models can be based on observations performed on a statistical sample for a variety of populations, e.g. gender groups, ethnicities, age groups, genetic groupings, etc. The present technology can involve using the immune-response prediction models to predict actual immune-response for a user by examining activity data and user demographic data. For example, changes to mobilization and clearance rates of immune cells and progenitors, changes in immune cell proteins and surface structure, expression of ribonucleic acid (RNA), etc. can all be predicted by examining combinations of activity exertion level, exercise heart rate, resting heart rate, difference between resting heart rate and exercise heart rate, time of exercise, time of day, intrinsic physical parameters such as age and gender, etc and applying the examined data to a prediction model.

Some embodiments of the present technology involve creating general predictions of immune-response for a given activity using population averages combined with personal data, such as height, weight, gender, and age. The prediction of a user's mobilization can be further optimized by collecting data points of actual mobilization, to account for inter-individual variation in the effects of various modulations. To achieve more personalized mobilization models, some embodiments of the present technology involve obtaining and analyzing personal genetic information and blood analysis data from one or more blood draws and using the analyzed data to optimize predictions, quantify results, etc., as explained in greater detail below. Similarly, a change in rate of the turnover of T cells and/or natural killer (NK) cells observed from actual post-activity blood draws can provide further data points.

After collecting data for a statistical population, an immune-response prediction model can be created in a clinical setting and can be used to provide others in the same or similar populations with a prediction about how the same or similar activity will affect their own immune-response.

FIG. 1 illustrates a system 100 providing users with information relating to how activity can affect their immune health based on clinically created immune-response prediction models and actual quantified user blood sample data. The system 100 includes a device 101 having a display 102, a processor 108, memory 110, a prediction engine 106, and a communication interface 114. The device 101 is also associated with an input device. For example, the display 102 can comprise a touch-sensitive display that acts as an input device itself.

The memory 110 stores instructions that, when executed by the processor 108, cause the device 101 to display one or more user interface elements $104_a$, $104_b$, ... $104_n$ that can be used to receive user information (e.g. age, weight, ethnicity, health status, gender, circadian rhythm data, etc.). The user information can relate to factors that have been clinically shown to correlate to blood cell mobilization or proven to cause changes to blood cell mobilization.

In some cases, user information can be received from the records of a health care professional (e.g. a doctor, a clinician, a fitness professional, etc.) For example, during an office visit, a user device can be used to download the information from the health care professional's computer system on to the device 101. Also, a healthcare professional can pre-load the device 101 on behalf of a patient and request, or prescribe, that the user begin using the device 101 (e.g. wearing a activity tracker, carrying a pedometer, etc.) to track immune-response. Similarly, a patient can authorize a doctor or clinician to release user information (including blood sample data, personal genetic data, etc., as explained in more detail below) to an immune-response modeling entity (described in more detail below) and the immune-response modeling entity can customize a device for the user, establish an account with the user, store activity data for the user, track blood cell mobilization after blood sample analysis, etc.

The system 100 can also store one or more clinically-created immune-response prediction models in memory 110, or the communication interface 114 can request, from an immune-response modeling entity 116 via a network 122, the one or more clinically-created immune-response prediction models. Also, the prediction engine 106 is configured to cause the processor 108 to create a personalized immune-response model based on a clinically-created immune-response prediction model and based on the user information received for the user. In some embodiments, the device 101 transmits, using the communication interface 114, the user information to an immune-response modeling entity 116.

The prediction engine 106 is further configured to cause the processor 108 to identify, based on the personalized immune-response model, an activity that is predicted to produce a blood mobilization response for the user. In some cases, user interface elements $118_a$, $118_b$, ... $118_n$ can be displayed to represent the activities, show the predicted blood mobilization responses, recommend an activity, etc. The processor 108 can also cause the device 101 to display a graphical representation of a predicted effect that the activity will have on mobilization of blood cells. Examples of graphical user interfaces for displaying immune-response information on portable electronic devices and wearable activity tracking devices are described below.

The device 101 can also include an activity tracker 112 coupled with the processor 108 and configured to receive activity data from the user that describes a user activity. For example, the activity tracker 112 can track data from a heart rate monitor. The activity tracker 112 can receive activity data from an activity sensor integrated within the device 101, from an activity sensor wirelessly coupled with the device 101 (e.g. a smart watch), from a network location via the communication interface 114, etc. Examples of activity sensors are described below or will be apparent to those with ordinary skill in the art having the benefit of the present disclosure.

The prediction engine 106 is further configured to cause the processor 108 to determine, based on the personalized immune-response model and the user activity data, a predicted effect that the activity data is predicted to have on the predicted blood mobilization response. In some embodiments, the prediction engine 106 is further configured to cause the processor 108 to display a new user interface element (not shown) or one or more of the user interface elements $118_a$, $118_b$, ... $118_n$ based on received activity data predicted effects on the personalized immune-response model. For example, when an activity tracker 112 determines that a user has sustained an optimal heart rate for suggested activity for a predetermined period of time, a user interface element 118a can be modified to display an update on the user device indicating how a user is progressing with a recommended activity that predictively addresses a specified immune-related goal.

Some embodiments of the present technology also involve modifying the personalized immune-response models based on quantified blood sample data from one or more blood draws. For example, a user can provide a blood sample after an activity that was observed by the activity tracker 112. The blood sample can be analyzed (e.g. using a cytometric assay) by a blood sample analysis entity 124 and the communication interface 114 can receive a message that blood sample data is available for download. After receiving the message, the processor 108 can cause a user interface element 120 to be displayed that requests that the user both authenticate himself and provide consent to the downloading of the blood sample data. After the user authenticates himself and provides consent, the processor 108 causes the communication interface 114 to download the blood sample data from the blood sample analysis entity 124 via a network 122.

The prediction engine 106 is further configured to cause the processor 108 to determine, based on the blood sample data, a correlation between the user activity and an actual blood mobilization response observed in the blood sample data. After a correlation is observed, the prediction engine can modify the personalized immune-response model based the correlation between the user activity and the actual blood mobilization response. The blood sample data, the activity data, and the correlation between the user activity and an actual blood mobilization response observed in the blood sample data can also be stored in memory for further future analysis, machine learning, etc.

In some cases, multiple, connected devices can be used to receive user data, track activity, provide user feedback. Also, the feedback may have different time intervals. For example, a user device can be configured for end-of-day reporting, end-of-week reporting etc., instead of or in addition to instantaneous feedback. Also, with a user's consent feedback reporting can be delivered to third parties, e.g. a doctor, an employer, an insurance payer, etc.

FIGS. 2A-2E illustrate examples of graphical user interfaces for displaying immune-response information on portable electronic devices and wearable activity tracking devices according to some embodiments of the present technology.

Figure 3:
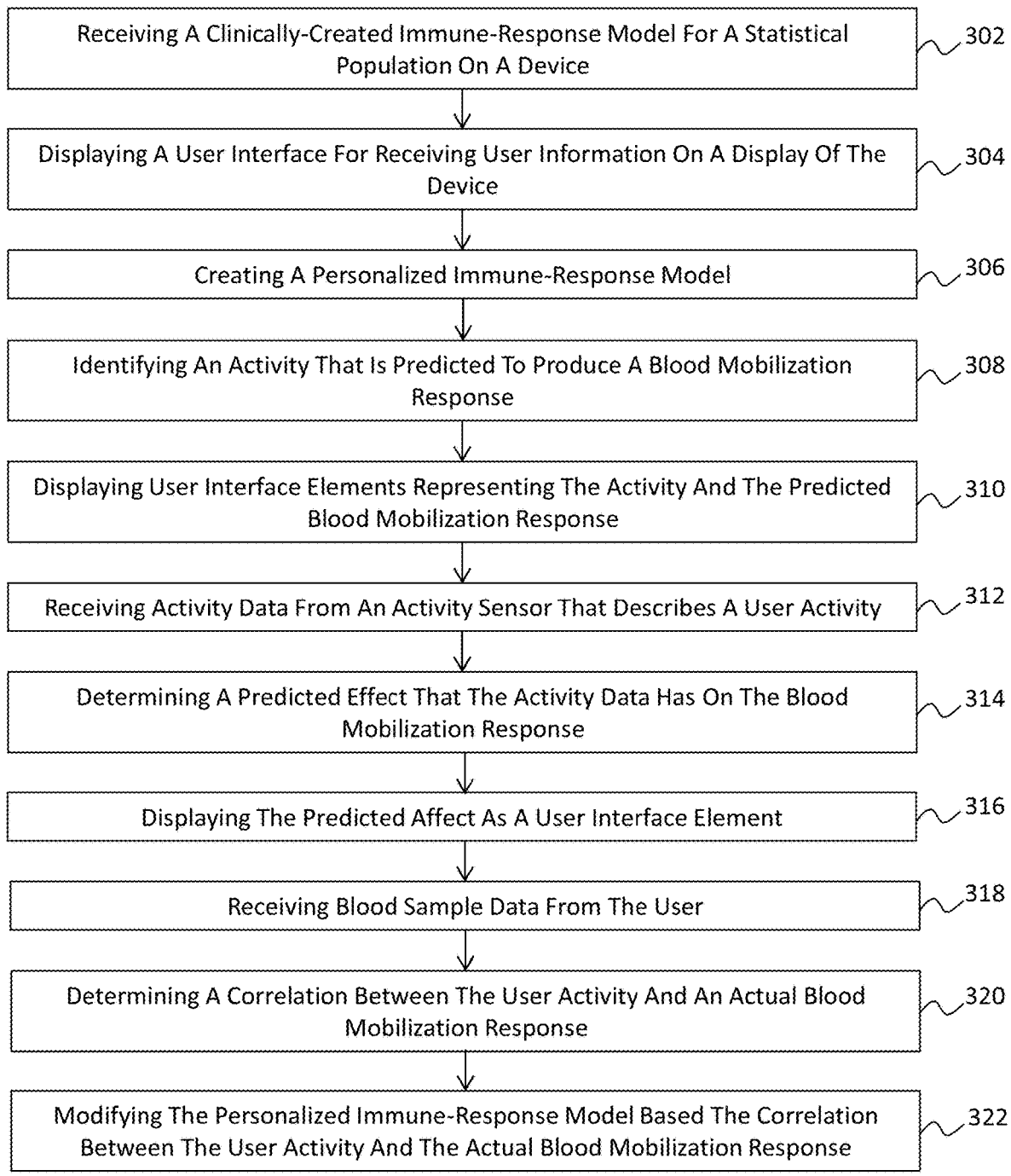
FIG. 3 illustrates a method of providing user devices with personalized information relating to immune-response according to some embodiments of the present technology.

FIG. 3 illustrates a method 300 of providing users with personalized information relating to immune-response according to some embodiments of the present technology. The method 300 involves receiving, on a device, a clinically-created immune-response prediction model for a statistical population 302 and displaying a user interface for receiving user information 304 on a display of the device. Next, the method 300 involves creating a personalized immune-response model based on the clinically-created immune-response prediction model and based on the user information 306. Also, the method 300 involves using the personalized immune-response model to identify an activity that is predicted by the clinically-created immune-response prediction model to produce a blood mobilization response for users in the statistical population 308. Also, the method 300 involves displaying one or more user interface elements representing the activity and the predicted blood mobilization response 310.

Next, the method 300 involves the device receiving activity data from an activity sensor that describes a user activity 312. For example, the device can include one or more activity sensor itself or the device can receive activity data from an activity sensor in another activity tracking device (e.g. wirelessly from a wearable activity sensor). Also, the method 300 involves determining a predicted effect that the activity data has on the blood mobilization response 314 based on the personalized immune-response model and the activity data. Next, the method 300 can involve displaying the predicted effect as a user interface element 316.

In addition to applying user information to a clinically-created immune-response model to form a personalized immune-response model, the method 300 can also involve receiving blood sample data 318 from the user to use actual cell mobilization data to modify the personalized immune-response model. For example, blood sample data can be derived from a baseline blood sample from the user and a blood sample obtained from the user after the user performed the user activity. The method 300 can also involve determining, based on the blood sample data, a correlation between the user activity and an actual blood mobilization response observed in the blood sample data 320 and modifying the personalized immune-response model based the correlation between the user activity and the actual blood mobilization response 322.

A general prediction of mobilization for a given activity is possible, using population averages combined with personal data, such as height, weight, sex, or age. However, the prediction of a user's immune-response can be optimized by collecting data of actual mobilization because there is significant inter-individual variation in the effects of various mobilization modulations.

In addition to modifying a user's personalized immune-response model based on user activity data and actual blood mobilization response following the activity, some embodiments of the present technology involve an immune-response modeling learning engine that takes advantage of a distributed user base that consents to allowing their user data and blood sample data to be used to refine immune-response prediction models.

Figure 4:
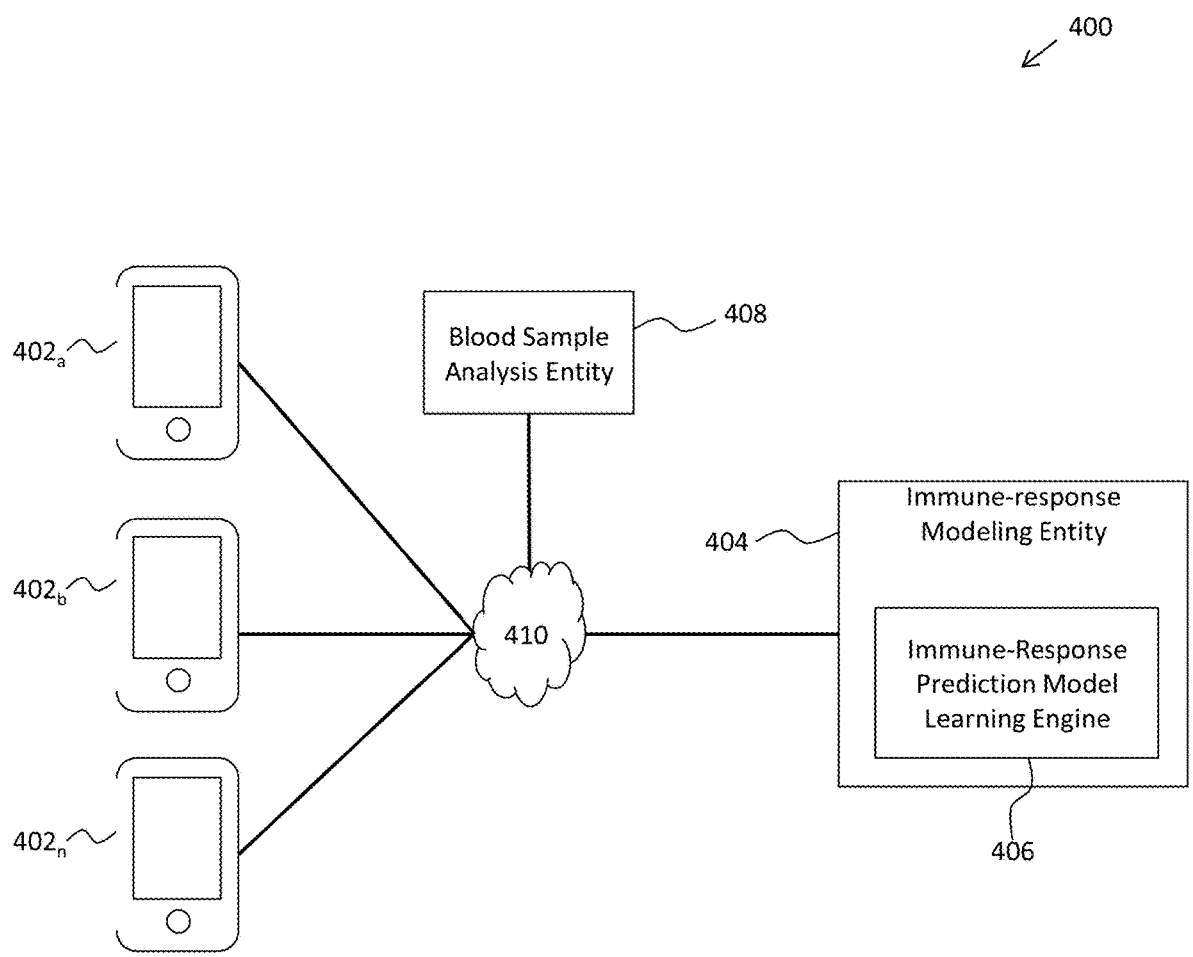
FIG. 4 illustrates a system for refining clinically-created immune-response prediction modules using data from a distributed plurality of users.

FIG. 4 illustrates a system 400 for refining clinically-created immune-response prediction modules using data from a distributed plurality of users. The user can opt-in to sharing personal information, activity data, and blood sample data and the shared data can be used to identify new insights and refine clinically created immune response models.

The system 400 includes an immune-response modeling entity 404 that uses clinical observations for a statistical population of participants to initially create an immune-response model and to further refine the immune-response model based on user feedback. The immune-response modeling entity 404 can distribute the clinically-created immune-response model to a plurality of user devices $402_a$, $402_b$, ..., $402_n$ that are connected to the immune-response modeling entity 404 via one or more network 410. Each of the plurality of user devices $402_a$, $402_b$, ..., $402_n$ can gather user information, activity data, and blood sample data from one or more blood sample analysis entity, personal genetic information, etc. Also, each of the plurality of user devices $402_a$, $402_b$, ..., $402_n$ can use the gathered data to personalize the predicted immune-response models for a particular user. Also, each of the plurality of user devices $402_a$, $402_b$, ..., $402_n$ can use blood sample data to refine, for the particular user, the predicted immune-response models.

Additionally, users who opt-in to sharing their personal immune-response information can transmit the information back to the immune response modeling entity 404. The immune response modeling entity 404 can also include an immune-response prediction model learning engine 406 that can use the personal immune-response information from the distributed user base to refine the initial immune-response prediction models. For example, statistical population can be expanded to include the collected personal immune-response information when clinicians associated with the immune response modeling entity 404 are confident that the gathered information is accurate. Also, machine learning algorithms can be employed to refine immune-response prediction models based on the gathered user information, activity data, blood sample data, personal genetic data, etc.

In addition to the above, some embodiments of the present technology involve creating a baseline recommended activity regimen for a user (e.g. to target one or more immune-related effect) based on clinical observations of a statistical population. For example, a user can input an immune-related goal (e.g. mobilization of white blood cells to combat a viral infection) and user information and an immune-response prediction model and create and display a baseline recommended activity regimen that is observed to achieve the specified goal. Also, an activity sensor can receive activity data that describes a user's activities and provide feedback to the user regarding whether their activity indicates will accomplish their immune-related target goal.

Figure 5:
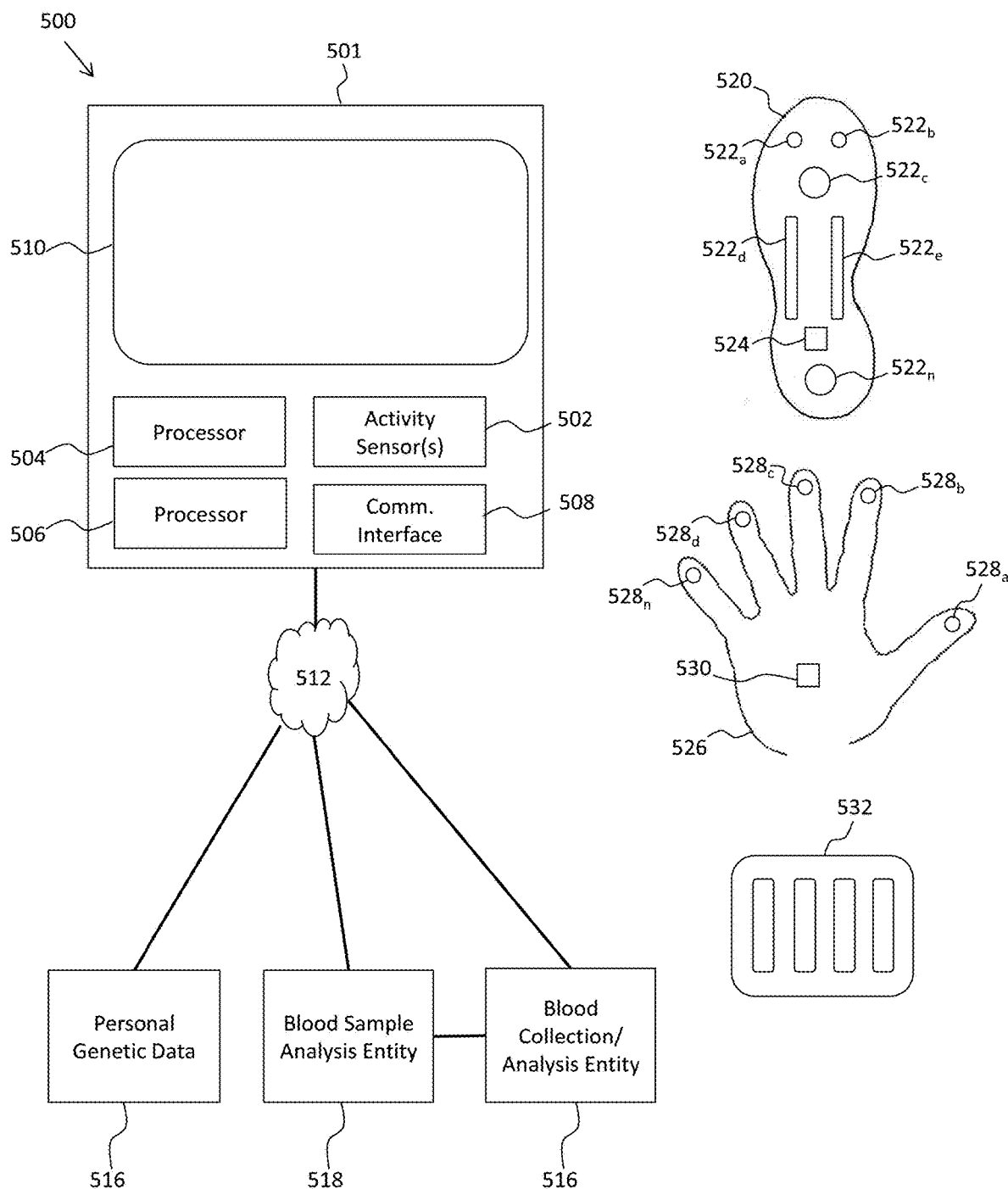
FIG. 5 illustrates a system for personalizing an immune-response prediction model using activity data, user information, and blood sample data according to some embodiments of the present technology.

FIG. 5 illustrates a system 500 for personalizing an immune-response prediction model using activity data, user information, and blood sample data according to some embodiments of the present technology. The system 500 includes an activity tracking device 501 that includes one or more activity sensors 502, a processor 504, and memory 506. The activity tracking device 501 can also involve a communication interface 508 for transmitting information from the activity tracking device 501 and for receiving information from other sources.

The activity sensors 502 can include one or more of a heart rate monitor, an accelerometer, a blood pressure monitor, an external temperature monitor, a body temperature monitor, a location tracking system, a pressure sensor, a skin conductance sensor, a blood oxygen level sensor, non-invasive glucose monitors, and a wide variety of other sensors that will be apparent to those with ordinary skill in the art having the benefit of this disclosure.

The activity sensors 502 receive activity data from a user and the activity sensors 502 can be coupled with the processor 504 and the memory 506. The memory 506 stores instructions that, when executed by the processor, cause the activity tracking device 501 to provide feedback to the user regarding a predicted effect their activity will have on blood cell mobilization. The activity tracking device 501 can process the gathered activity data using an immune-response prediction model describing how activity affects the mobilization of blood cells. The activity tracking device 501 can store (e.g. in the memory 506) the immune-response prediction models. The activity tracking device 510 can also obtain (e.g. via the communication interface 508) immune-response prediction models from another source, e.g. a network location.

The processed activity data can be presented to the user as raw data (e.g. heartrate, time exercised, etc.), as one or more charts, etc. Also, the mobilization prediction models can further be used to create one or more recommended baseline activity regimen and the processed activity data can be compared against the recommended baseline activity regimen. For example, when creating an immune-response prediction model in a clinical setting a particular activity (e.g. running at a defined level, in defined increments, for a defined period of time) can be determined to more-effectively mobilize certain blood cells than other activities. This particular activity can be used as a recommended baseline activity regimen. Next, the processed activity data from the activity sensor can be compared recommended baseline activity regimen and the activity tracking device 501 can provide feedback to the user relating to their compliance with or deviation from the exercise regimen. For example, the activity tracking device 201 can be configured to display a notification or cause an auditory or haptic alert when the user activity data indicates a predetermined threshold deviation percentage (e.g. 20%) from the recommended baseline activity regimen.

The activity tracking device 501 can also include a display 510. The display 510 can also be associated with a user input. For example, the display 510 can be a touch-sensitive display that can accept touch gestures and can display a virtual keyboard as the user input. Also, the user input can include one or more of a keyboard, toggle buttons, a microphone and speech recognition software, and a wide variety of other user input devices that will be apparent to those with ordinary skill in the art having the benefit of this disclosure.

The display 510 can provide a graphical user interface (GUI) for presenting information to the user and for providing the user with interface elements for allowing the user to enter information. For example, the GUI can include interface elements for allowing a user to enter their age, weight, ethnicity, health status, gender, circadian rhythm data, etc. The GUI can also include interface elements for allowing a user to enter immunity-related mobilization goals, request consent to allow the activity tracker to obtain the user's blood sample data or personal genetic information, etc. User information can also be derived from a variety of other sources. For example, certain genetic information can be correlated to or inferred from a user's self-reported ethnicity. Also, in some embodiments, the activity tracking device 501 can include a camera and capture a user's physical traits (e.g. skin tone, eye color, etc.) and the activity tracking device 501 can correlate or infer certain genetic information from the traits.

When the user consents to allowing the activity tracking device 501 to obtain the user's blood sample data or personal genetic information, the activity tracking device 501 can request, via the communication interface 508, through a network 512, the information from one or more of a blood sample data repository 514, a blood collection and analysis entity, a personal genetic data repository 516, etc.

Blood sample data can be derived in a variety of ways, For example, some embodiments of the present technology involve deriving blood sample data from analyzing blood drawn from a user after the user has performed a specified activity and comparing the results (e.g. blood cell levels, blood cell types, etc.) to data collected for a statistical population. Blood sample data can also be derived from analyzing a baseline blood draw and comparing the results to an analysis of a blood sample obtained from the user after the user performed the specified activity.

In some embodiments of the present technology, the activity tracking device 501 can use the user information, blood sample results, personal genetic information, etc. to personalize the mobilization prediction models for specific user characteristics. The activity tracking device 501 can also refine the immune-response prediction model in response to the user entering a specific immunity-related mobilization goal. For example, an immune-response prediction model can also be refined to optimize the mobilization of selected blood cells for treating baseline immunity (e.g. to combat common viral infections), the mobilization of white blood cells after a chemo-therapy treatment, stimulating specific blood cells after vaccination to increase the effectiveness of the vaccination, etc. Furthermore, in some embodiments, the activity tracking device 501 can optimize the immune-response prediction model and/or activity regimen to increase one or more particular mobilization trait. For example, the activity tracking device 501 can create a personalized activity regimen that optimizes a mobilization stacking effect or avoids avoid alterations that negatively impacts the function of the immune system (e.g. a so-called overtraining effect as explained below). The creation and refinement of immune-response prediction models and activity regimen is explained in greater detail below.

The system 500 can also include one or more additional activity sensors for gathering additional activity data to further personalize the mobilization prediction models, recommended activity regimens, etc. For example, the additional activity sensors can include accelerometers, hear rate monitors, pressure sensors, etc. that are attached to a user's head, chest, thighs, ankles, etc. As shown in FIG. 5, the system 500 can include a shoe insert 520 that includes foot force measurement sensors $522_a$, $522_b$, ..., $522_n$ for measuring force exerted through a user's feet. The shoe insert 520 can also include a wireless communication interface 524 for transmitting force measurement data to the activity tracking device 501. Similarly, the system 500 can include a glove 526 that includes hand force measurement sensors $528_a$, $528_b$, ..., $528_n$ for measuring force exerted through a user's feet. The glove 526 can also include a wireless communication interface 530 for transmitting force measurement data to the activity tracking device 501.

In some embodiments, the system 500 also includes a blood collection kit 532 containing a blood collection apparatus, a blood preservation and storage unit, packaging for shipment to a lab, etc.

Figure 6:
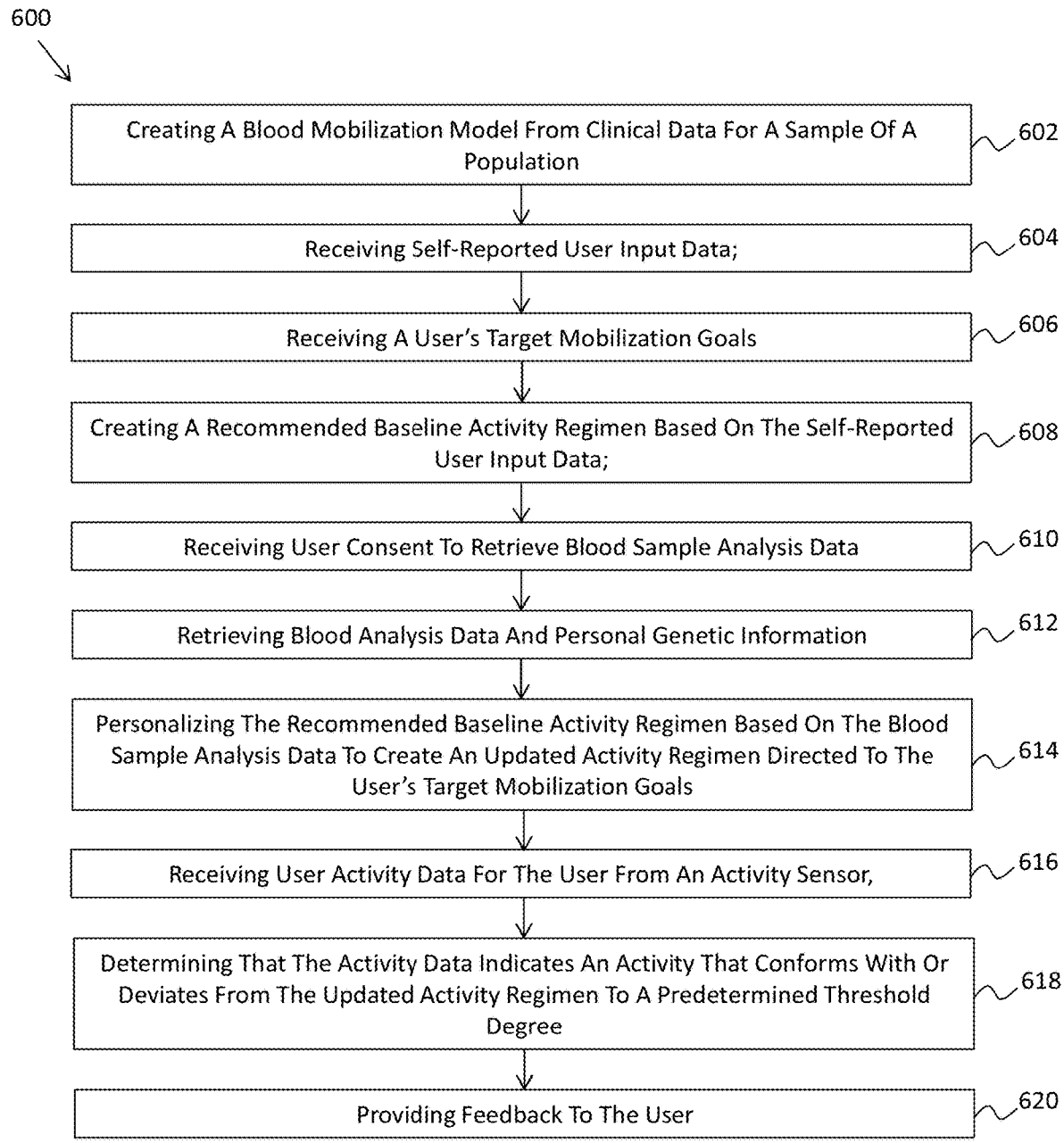
FIG. 6 illustrates a method of providing a user device with feedback regarding when an activity conforms with or deviates from a recommended baseline activity regimen according to some embodiments of the present technology.
Figure 7A:
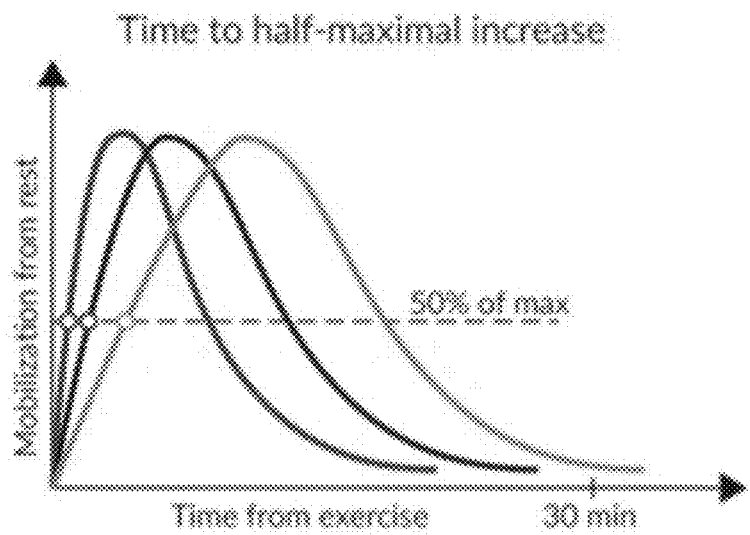
FIGS. 7A-7E illustrate example of short-term immune cell mobilization curves.
Figure 7B:
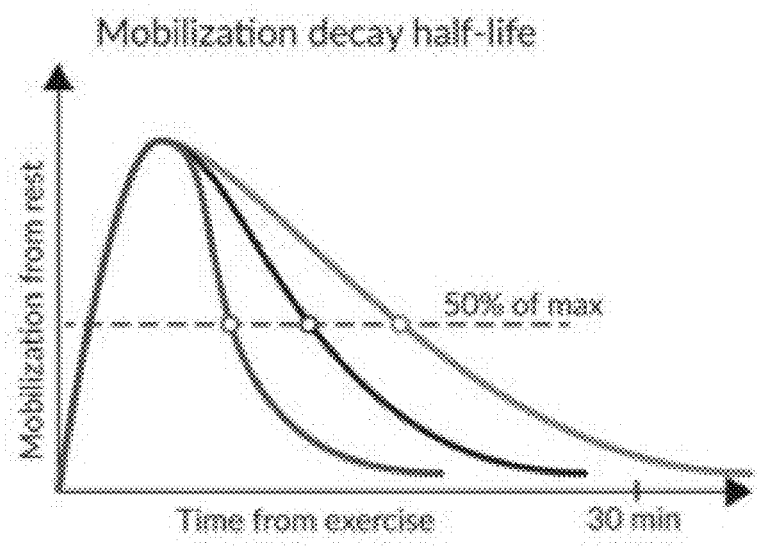
Figure 7C:
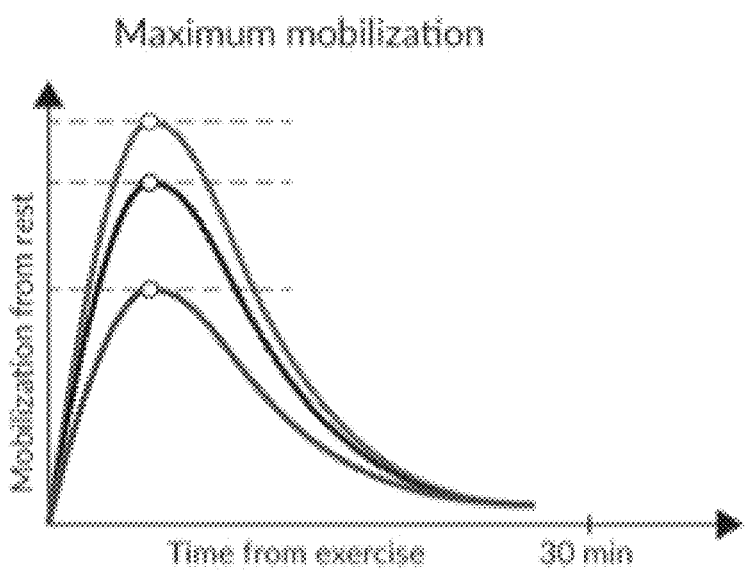
Figure 7D:
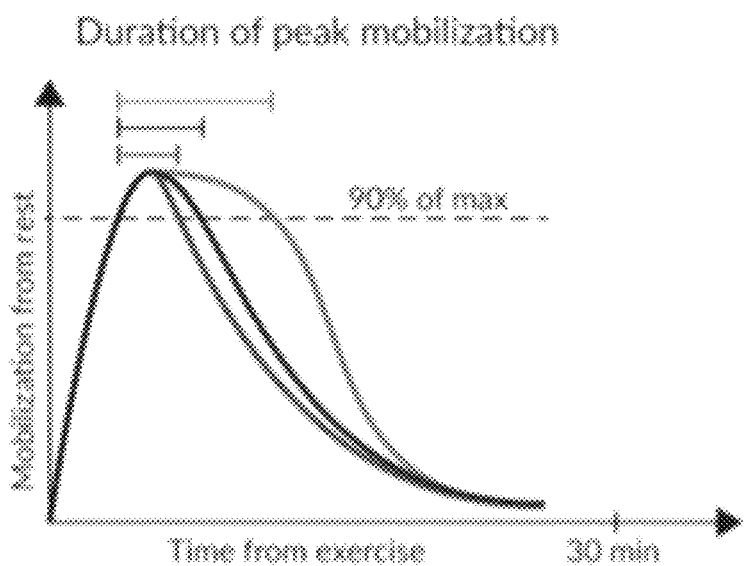
Figure 7E:
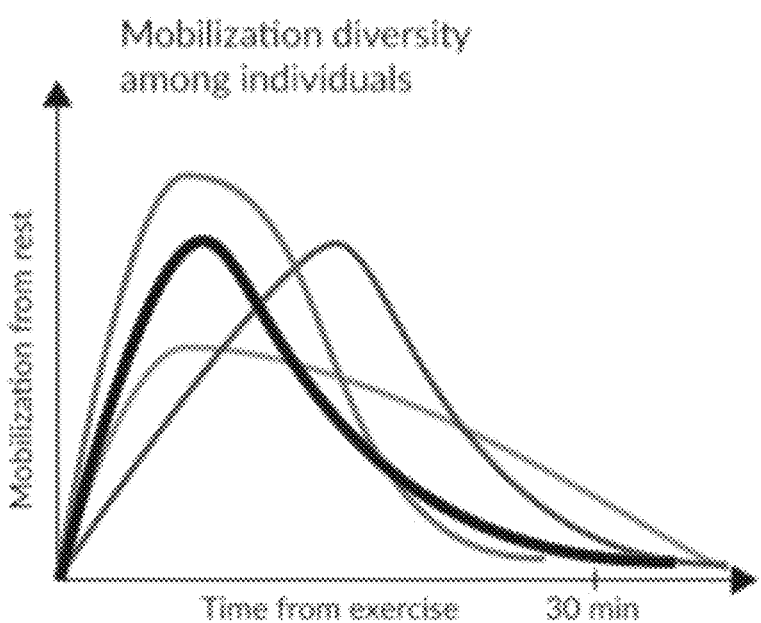
Figure 8A:
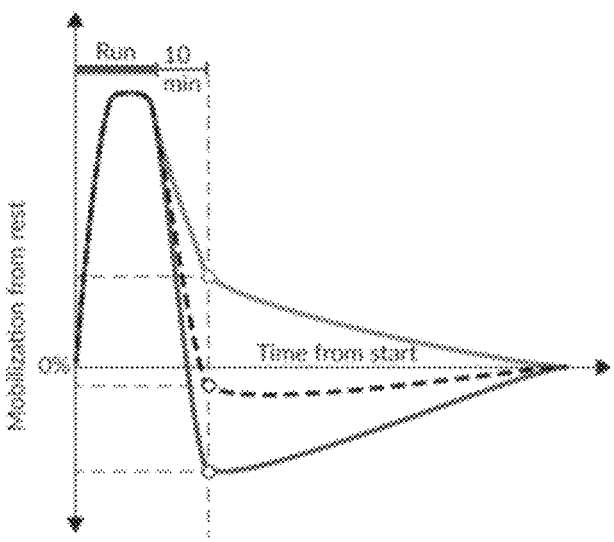
FIGS. 8A-8D illustrate example of medium-term immune cell mobilization curves.
Figure 8B:
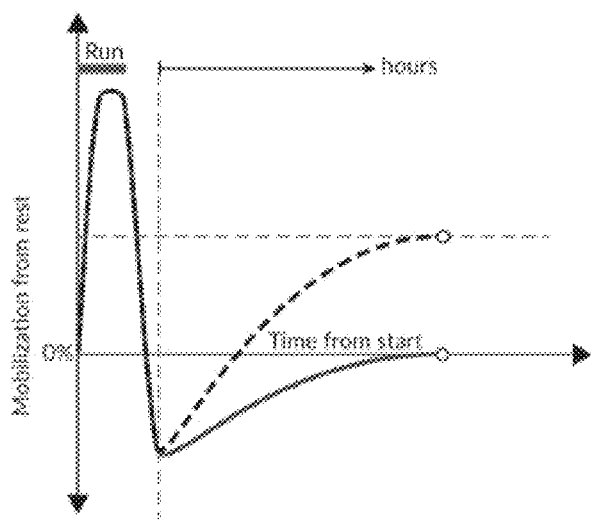
Figure 8C:
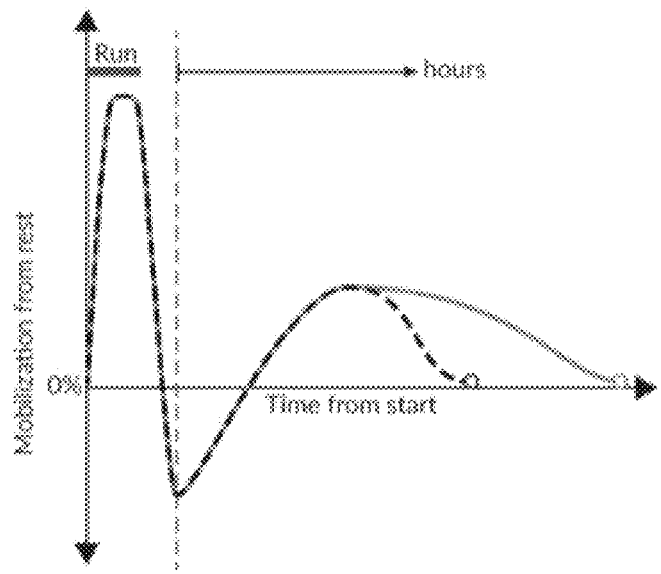
Figure 8D:
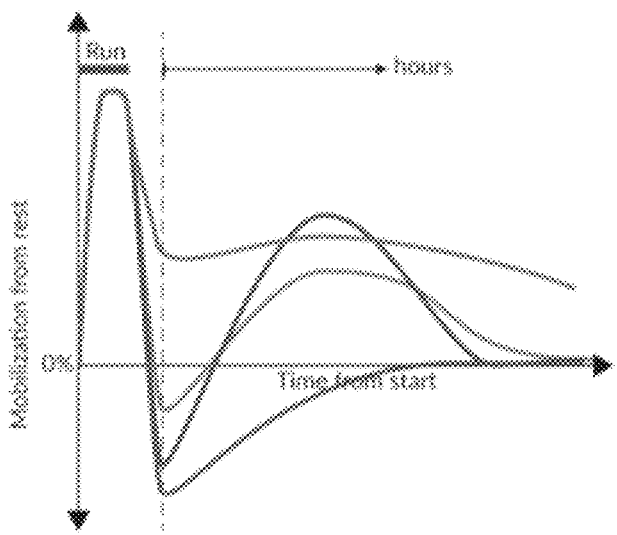

FIG. 6 illustrates a method 600 of providing a user with feedback regarding when an activity conforms with or deviates from a recommended baseline activity regimen according to some embodiments of the present technology. The method 600 involves creating a blood mobilization model from clinical data for a sample of a population 602, receiving self-reported user input data 604, receiving one or more of the user's target mobilization goals 606, and creating a recommended baseline activity regimen based on the self-reported user input data 608.

Next, the method 600 involves receiving user consent to retrieve blood sample analysis data 610, retrieving blood analysis data and/or personal genetic information 612, and personalizing the recommended baseline activity regimen based on the blood sample analysis data to create an updated activity regimen directed to the user's target mobilization goals 614.

Finally, the method 600 involves receiving user activity data for the user from an activity sensor 616, determining that the activity data indicates an activity that conforms with or deviates from the updated activity regimen to a predetermined threshold degree 618, and providing feedback to the user 620. For example, the feedback can involve the sending of a notification, the generation of a text message, an auditory or haptic alert, etc. indicating the conformance or deviation from the updated activity regimen.

According to some embodiments of the present technology, system utilizing predicted immune-response models, collected activity data, and blood sample data can also be used to influence the distribution of a particular immune cell throughout the body or more generally the entire immune system, to target particular immune functions, and to precisely time a stacking effect (explained in more detail below). Also, some embodiments of the present technology involve immune health programming that includes immune modulation protocols with specific health goals, such as mitigation of T-cell autoreactivity, or prevention of immune suppression during peak flu season. These programs can also be structured to achieve increases in cell types that have uses upon donation or banking, such as hematopoietic progenitors or red blood cells.

As explained above, some embodiments of the present technology involve creating, refining, personalizing immune-response predictions. Considerations taken into account when making such predictions involve understanding how to track activity. For example, for a given activity, such as running, the immediate (2-20 minute) mobilization of cell types is somewhat correlated to heart rate in beats per minute (BPM) with greater heart rate correlating with greater mobilization of most cell types. In some circumstances, heart rate can provide a primary parameter to predict short term mobilization (up to 1 hour post exercise). Therefore many embodiments of the present technology include a component of heart rate monitoring.

In some cases, heart rate is an accurate sole predictor of mobilization, e.g. when going from a long rest state (e.g. less than one hour) to a state of moderate activity. Longer exercise periods have more complicated and individualized patterns of circulating immune system change. In some cases, a model predicting current mobilization using current heart rate alone will not accurately predict even generalized peripheral immune system change in some situations. Mobilization is also influenced by an array of physiological factors, including physical and biochemical signals, that can work in concert or individually to produce a diverse set of mobilized states. A measure such as heart rate may correlate well with mobilization of some cell types at some points in some activities but not in others, sometimes necessitating a more-complex algorithm to comprehensively predict mobilization.

Some embodiments of the present technology also include selection of an exercise modality to achieve specific short-term mobilization goals since different types of exertion can induce physiological changes to different degrees. Furthermore, because various physiological effects of exertion last for different amounts of time and affect populations of cells differently, it is possible to tailor an exercise program to achieve specific medium- and long-term mobilization goals.

A wide variety of factors are considered when making correlations between heart rate and mobilization. For example, anaerobic exertion is considered because, in some cases, mobilization is induced without increasing heart rate, or to a magnitude disproportionate with the increase in heart rate. This can happen through a number of mechanisms, such as high muscular exertion without commensurate heart rate increase, physical alterations in body position that alter blood flow and pressure without producing exertion and changes in soluble signaling factors in the body. In some examples, focused, moderate anaerobic exertion, such as weight training, can lead to increases in mobilization.

In other cases, physically altering blood flow without exertion can lead to changes in mobilization. Various activities may induce these changes of blood flow: standing up, reclining with the legs above the heart, or performing a full inversion, such as a headstand. Other examples of mobilization without heart rate elevation can include stretching or massage, which can induce cytokine release due to mild muscle trauma. All these movement changes can be detected (e.g. using an accelerometer) and can be programmed into the system to enhance accuracy of daily mobilization trends.

A divergence from mobilization proportionality to heart rate is the suppression and rebound mobilization that can occur after exercise. For example, following a twenty minute run, heart rate rapidly returns to baseline. Concomitantly, peripheral blood cell numbers fall from their immediate term peak levels, with some cell populations' peripheral numbers suppressed even below baseline for a short period. Following this suppression, suppressed cell types' numbers rise over a period of several hours and surpass baseline. Throughout this period, heart rate remains constant. Thus to correctly predict circulating cell numbers, the predictive engine will use past heart rate and exertion information.

Measurement of heart rate depends on the device used. Therefore, some embodiments of the present technology involve combining heart rate measurements from a pulse-monitoring device with exertion measures calculated from accelerometer data to increase the confidence in the measured data and resulting mobilization prediction. As technologies to measure physiological change improve, the prediction model can be updated to improve precision and accuracy of the results.

Predicting immune-response can also involve accounting for changes in cardiovascular fitness and/or oxygen carrying capacity of blood due to exercise. Regular exercise has a number of effects on the increase in heart rate relative to a given level of physical work output. In general, physiological changes such as increased cardiac strength and output, increased numbers of red blood cells per unit volume of blood, and increased hemoglobin per red blood cell result in altered heart rate for a given amount of muscular effort. Given that users will be engaging in regular physical activity, accounting for these changes is important for the accurate correlation of mobilization and heart rate increases. Likewise, accounting in changes to resting heart rate can be compensated for as a person's level of fitness changes over time.

Accounting for blood system fitness can be accomplished using sensor-based, prompt-based, and biological sample-based methods. Monitoring of resting heart rate, heart rate change during a quantified exertion, such as a 100 m sprint over flat ground, or time required to run a mile on flat ground are examples of sensor-based methods of quantifying blood system fitness. Prompting the user to use a treadmill to run a mile at their maximum speed and then enter the time required is an example of prompt-based quantification. Acquiring baseline hematocrit and hemoglobin numbers, either through a submitted sample or through an outside lab is an example of biological sample-based methods.

Some embodiments also involve collecting data to predict mobilization in real time. In many exertion scenarios, heart rate provides a key parameter to predict mobilization. Consequently, a fitness tracking device with the ability to measure heart rate can be a key component of this system. It is important that heart rate is accurately measured, with fine time resolution, since changes in mobilization can occur with small changes in heart rate, and can happen in time periods less than a minute. Many day-to-day mobilization scenarios, such as climbing a single flight of stairs, will increase heart rate and can produce measurable change in circulating and resident immune cell levels, changing system predictions for some time. Consequently, in some cases, a heart rate monitor has a form factor that all-day wear is not an undue burden to the user. A watch form factor, measuring heart rate with skin reflectivity, can be ideal for this characteristic. In addition to using physics-based exertion quantification (discussed below), chest strap monitors that detect the electrical activity of the heart may be more suited to this type of exercise. The system can also incorporate multiple heart rate monitors, as well as other measurements, to cross-validate and improve confidence in any heart rate data.

Some embodiments also involve using physics-based exertion quantification. For example, many day-to-day mobilization scenarios can be predicted better using a heart rate monitor in concert with an accelerometer, and a global positioning system (GPS). The accelerometer, in combination with entered weight, can be used to calculate energy expended during movement. The GPS can provide additional data on rate of movement. Combining these data, exertion from activities such as walking or running on flat ground or inclines, bike riding, or climbing stairs can be easily identified, as can periods of inactivity. By automatically identifying and tracking the most common fitness activities, the automatic collection of exertion data can reduce the need to enter information throughout the day.

Some embodiments also involve predicting mobilization during weight training. For this type of exertion, two complementary tracks can be suggested: In an eemplary first track, a standardized routine is performed that will lead to predictable levels of muscle fatigue and anaerobic respiration. By combining this with concomitant heart rate monitoring, a reasonably accurate mobilization profile can be obtained. A second exemplary track incorporates additional sensors to specifically track exertion, through measures such as skin conductance, blood pressure, physical measurements, pressure sensors and/or enhanced accelerometer algorithms.

Some embodiments also involve combining subjective experience for more accurate predictions. For example, in addition to collection of quantified data, subjective descriptors of exertion, such as "tiredness," "soreness," and "exhaustion," can be combined with the objective measures to gain a fuller picture of exertion. Given that these subjective experiences have some physiological correlates, prompting the user to provide measures of these factors may improve the prediction of mobilization. This can be as simple as a post-exercise questionnaire in the application or on the fitness tracker asking the user to rate these subjective descriptors on a scale of one through ten.

Predicting immune-response can also involve examining cell mobilization over a period of time before, during, and after activity. Mobilization occurs on at least two time scales of significance: short-term and medium-term. Short-term mobilization encompasses the initial change in cell numbers leading up to and within 20-40 minutes following a period of exertion. Medium-term mobilization describes the effects occurring between short-term and up to 12 hours following exertion. Effects lasting longer than twelve hours could be termed immune system modulation for discussion purposes, reflecting a lasting change to the peripheral immune system, rather than a temporary occupation of the circulation by stored immune cells.

One possible set of data inputs to the prediction model can be either exertion calculated in real time, using personal information entered by the user (e.g. such as age, weight, etc.) combined with real-time measurement of exertion calculated from a heart rate monitor, accelerometer and GPS data, or a pre-set routine that is selected by the user and then monitored using the same sensors.

To describe the shape of most immune cell mobilization curves, the short- and medium-term mobilizations can be described with four and three characteristics, respectively. FIGS. 7A-7E illustrate example of short-term immune cell mobilization curves. The immune cell mobilization curves include time to half-maximal increase, mobilization decay half-life, maximum mobilization magnitude, and duration of peak mobilization. (A) The timescales for half-maximal mobilization and (B) decay of mobilization allow prediction of how quickly a population of cells will be mobilized, and how long following cessation of exercise the cells will stay mobilized to a given degree. The maximum mobilization (C) varies from individual to individual, and among cellular subsets. For a given mobilization, this maximum is largely correlated to exertion. However, recent prior exercise is a strong modifier of mobilization effect. Finally, the length of time an individual's cells remain at maximal mobilization (D) varies from person to person, and has a great impact on the correlation between exertion input and mobilization output. (E) Using these four parameters, a wide array of short-term mobilization curves, encompassing most individuals' mobilization responses to a brief mobilization, can be specified.

FIGS. 8A-8D illustrate example of medium-term immune cell mobilization curves. Medium-term mobilization (for a single activity session), in one programming model, can be described by a minimum of three characteristics, as shown in the figure above: Immediate suppression magnitude, secondary magnitude, and secondary duration. (A) Immediate suppression magnitude describes the difference between baseline cell numbers and cell numbers within the 10-30 minutes following an exertion such as a run. Cell numbers may fall below baseline, or remain above baseline. (B) Secondary magnitude is the point to which cell numbers rebound following the post-exertion suppression. (C) Secondary duration is the amount of time cell numbers remain elevated following the rebound. This time period will often last a significant number of hours. (D) Combining these three characteristics, the medium-term mobilization of multiple cell types can be described.

A select group of inputs can describe a large portion of the quantitative and qualitative differences in mobilization of a given cell type for a given individual, including exertion intensity, exertion duration, personal characteristics, and cell type.

Exertion intensity can be an important factor in cell mobilization. For example, when running on a treadmill, increasing the speed and incline increase the intensity. Each person has a maximum exertion intensity for a given exercise modality. Also, exertion duration can be an important factor in cell mobilization. Exercising at maximum intensity for two minutes has both qualitative and quantitative differences from exercising at maximum intensity for twenty minutes. Exertion intensity is not necessarily constant throughout the duration of a period of exercise. Tracking of heart rate can be partially used to fine-tune this input. Cell type is an important factor in cell mobilization since each cell type has a different short- and medium-term mobilization profile. Also, personal characteristics (age, weight, health status, circadian rhythm etc.) affect mobilization of many cell types.

Figure 9A:
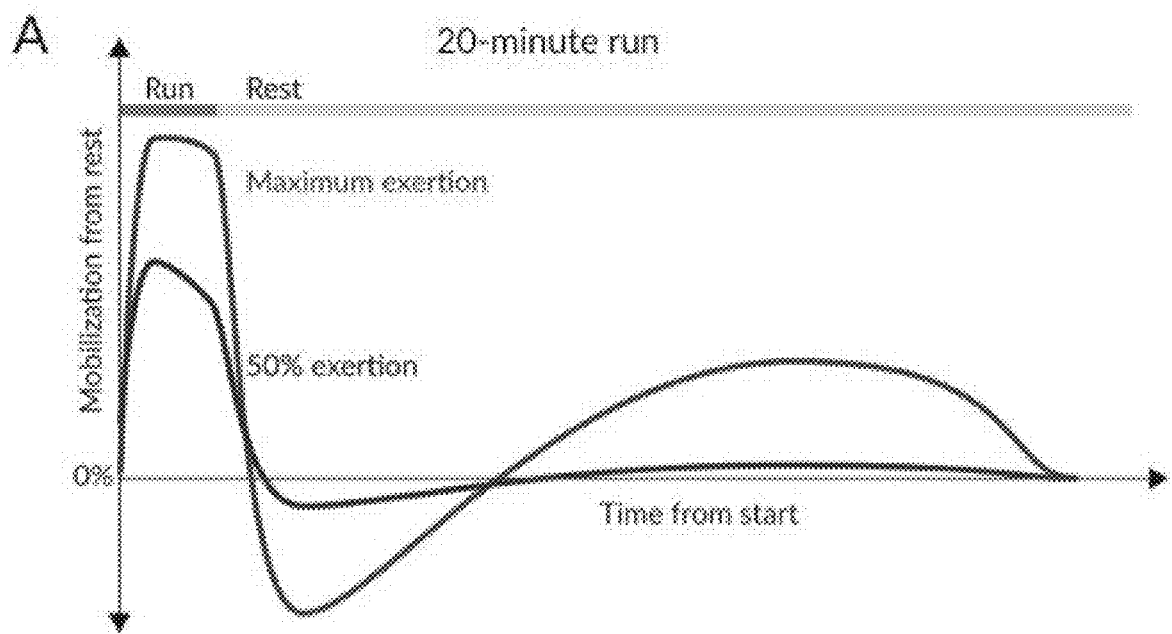
FIGS. 9A and 9B illustrate examples of how exercise intensity and duration effect cell mobilization.
Figure 9B:
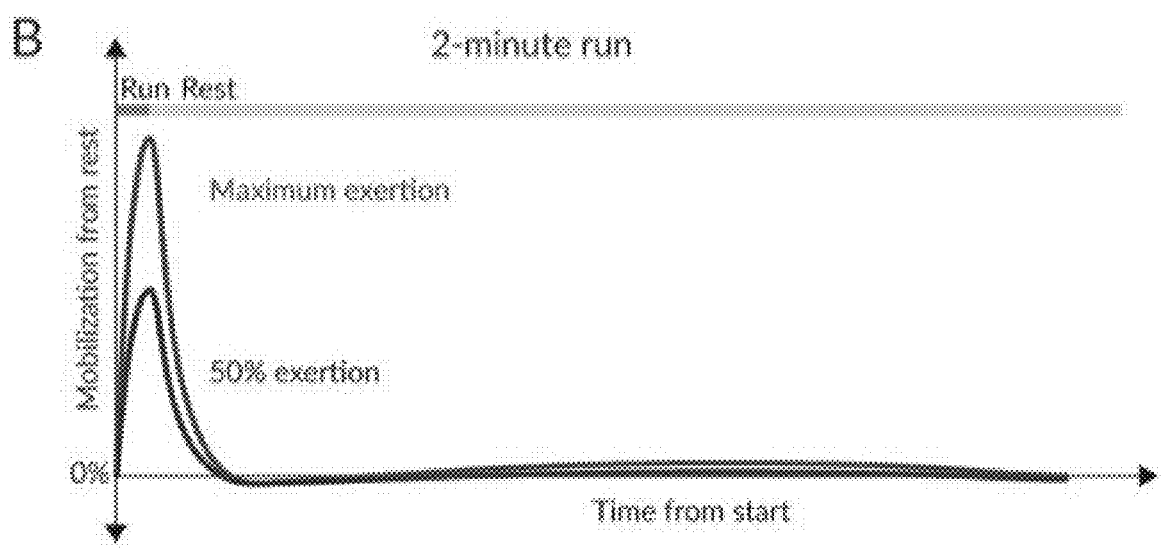

Additionally, exertion intensity and duration can affect both the short- and medium-term characteristics of mobilization curves. FIGS. 9A and 9B illustrate examples of how exercise intensity and duration effect cell mobilization. In general, lower exertion appears to produce lower short-term mobilization, regardless of duration. Longer duration exertion, however, has non-linear effects on medium-term mobilization. Whereas a 2-minute run at maximum exertion generally produces a single mobilization spike, a 20-minute run at high exertion can produce a spike, a suppression, and then a rebound mobilization lasting hours after cessation of exertion.

Figure 10:
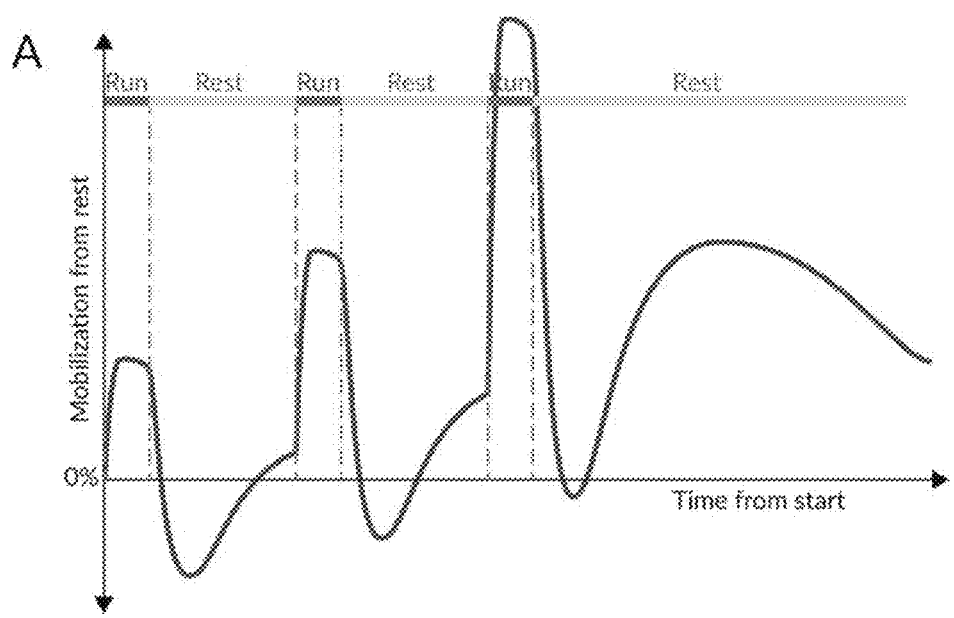
FIG. 10 illustrates a mobilization stacking technique according to some embodiments of the present technology.

Additionally, some embodiments of the present technology involve adding subsequent exertion periods, to "stack" mobilization, thereby combining the upswing of the medium-term mobilization with a short-term mobilization for an overall nonlinear gain in mobilization. FIG. 10 illustrates a mobilization stacking technique according to some embodiments of the present technology. The stacking effect can be used in a number of ways, such as when preparing to donate cells. Importantly, a generalized or individualized computer-based mobilization program using mobilization stacking effects can be used to capture cells that, at baseline or with even a single mobilization, are not present to sufficient levels for a particular application. Mesenchymal stem cells are an important cell type that fits into this category, depending on other variables such as age and health status.

Also, because timing of medium-term mobilization varies between cell types, enhancement of one cell type's mobilization, in some cases, may actually suppress another's mobilization. Therefore some embodiments of the present technology involve strategically enhancing mobilization of one or more desired cell type. In some cases, one cell type being mobilized will not suppress another directly and the effects can occur simultaneously to varying degrees.

Figure 11:
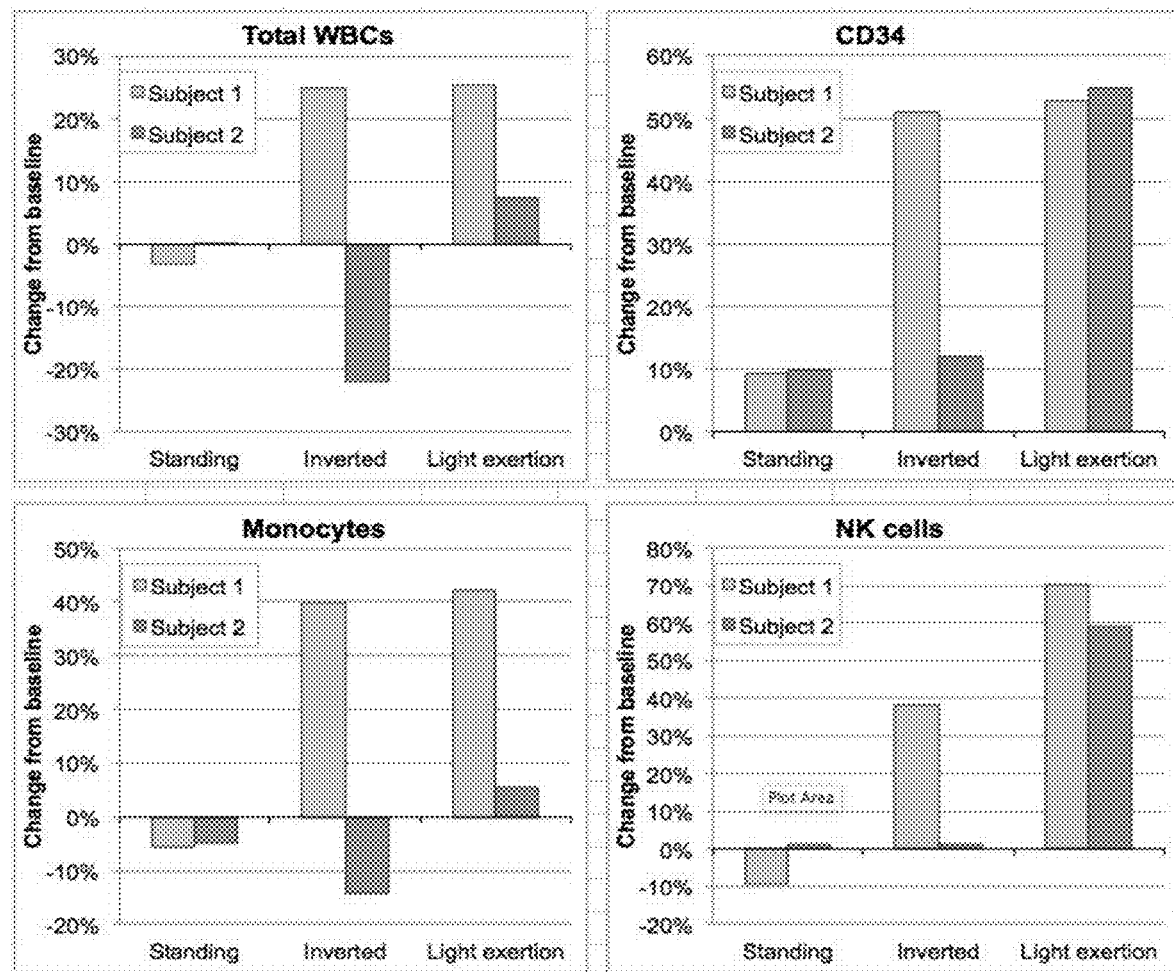
FIG. 11 illustrates a series of charts showing significant differences in immune-response for two subjects.

As explained above, actual blood sample data for obtaining personalized blood cell counts optimizes prediction of immune-response. FIG. 11 illustrates a series of charts showing significant differences in immune-response for two subjects. FIG. 11 shows relative mobilization of total white blood cells and three different cellular subsets—CD34+ cells, monocytes, and NK cells—enumerated in two individuals performing identical routines. Though CD34+ cells' and NK cells' mobilizations are relatively similar following light exertion, the effect of light exertion on monocytes is significantly different. More strikingly, the effects of inversion are dissimilar in all cases, and even move overall CD45 cell numbers in opposite directions in the two subjects.

There are many possible implementations blood sampling. For example, the blood can be collected by the user or by a medical professional, and then shipped, dropped off, or analyzed in-house. Some blood sampling considerations can improve performance.

One blood sampling consideration involves the activity of the user prior to sampling being directed and/or tracked. For example, the user can directed to take a blood sample in the morning, before undergoing any significant exertion, following a period of sitting lasting thirty to sixty minutes. In an extension of this example, the user may then be directed to exercise for a pre-determined period and then provide additional samples. In another example, real-time heart rate and motion monitoring is used to ensure that the user has not undergone significant immune system change before an in-clinic blood draw protocol.

Another blood sampling consideration involves cells in blood being preserved in a manner that allows accurate enumeration and immunophenotyping. For example, blood can be analyzed immediately after drawing. When immediate analysis is not performed, the present technology can involve methods that preserve cell numbers and surface immunophenotype, such as a method involving chemical preservation of the blood for a longer period of time for shipping.

Another blood sampling consideration involves the volume of sampled blood being accurately determined. To acquire reliable mobilization counts, it can be important to have a reading of initial blood volume. In some embodiments, this can be accomplished, for instance, with a device that measures a defined amount of blood before mixing with other reagents. As another example, the blood may be preserved with additives that do not change the blood volume, allowing the volume determination to occur at the time of analysis.

Another blood sampling consideration involves blood being prevented from undergoing any major degradation. Clotting, activation of immune cells, cell death, or any significant change to the blood's physical makeup can alter the final analysis of the cells.

Blood samples can be collected in a variety of ways. For example, blood can be acquired by venipuncture in tubes containing Ethylenediaminetetraacetic acid (EDTA), collected from a finger prick, etc. The timing of blood draws can also be accounted for. For example, a baseline blood sample can be taken when the user has been sitting for a minimum of thirty minutes. Baselines can be affected by prior activity, so longer periods of inactivity are preferable if prior activity cannot be accounted for. An exertion mobilization blood sample can be taken after any amount of any activity that typically leads to an increase in heart rate along with mobilization, such as running, calisthenics, anaerobic exertion. An alternative mobilization blood sample can be taken after stretching, inversion, massage, or any activity that typically alters mobilization without increasing heart rate. A resting blood sample can be taken while a user is sitting at rest, following mobilization. In some cases, resting blood samples can be taken hours after the mobilization.

Some embodiments involve an in-clinic controlled blood sampling protocol and mobilization analysis where the user can be confirmed to be resting for an appropriate amount of time for a baseline, where the user's exertion can be similarly controlled (e.g. with a treadmill set to a defined speed and incline), and where blood samples are taken at precise timepoints during and after this exertion. Additionally, some embodiments of the present technology involve a kit for at home blood draws, preparation of stabilized blood sample for shipping, optimizing of blood sampling.

Figure 12A:
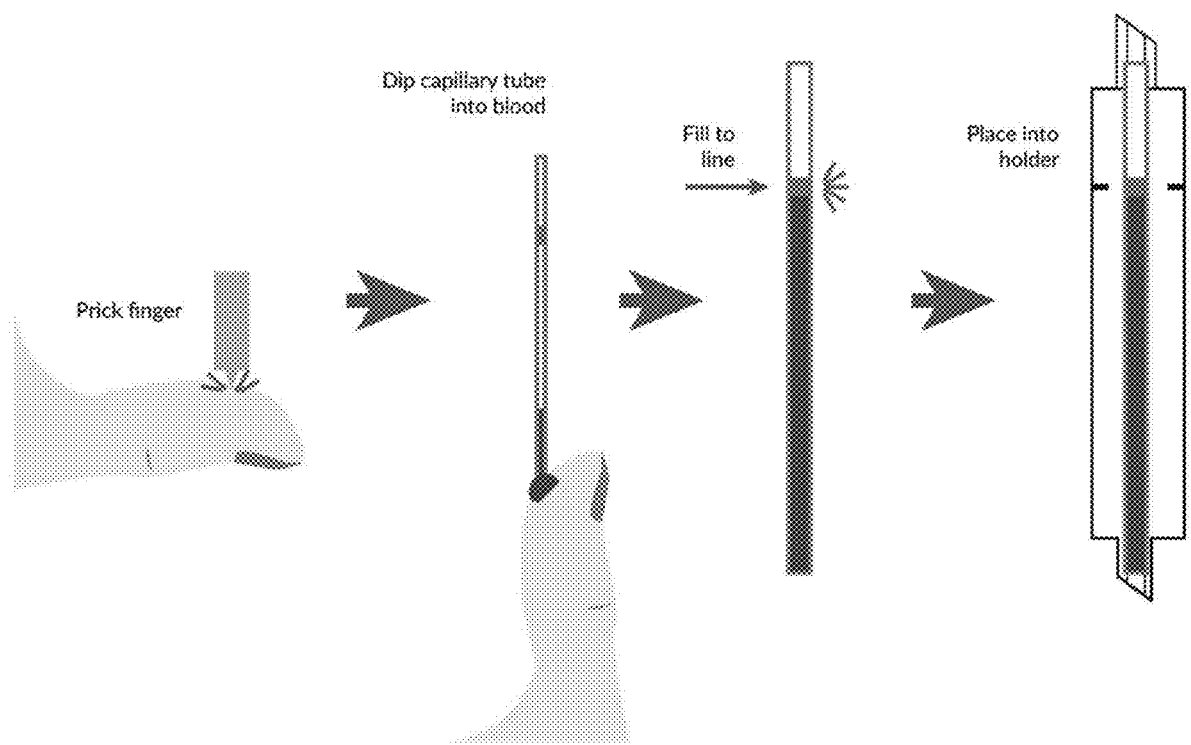
FIG. 12A-12D illustrate examples of a kit for taking blood samples according to some embodiments of the present technology.
Figure 12B:
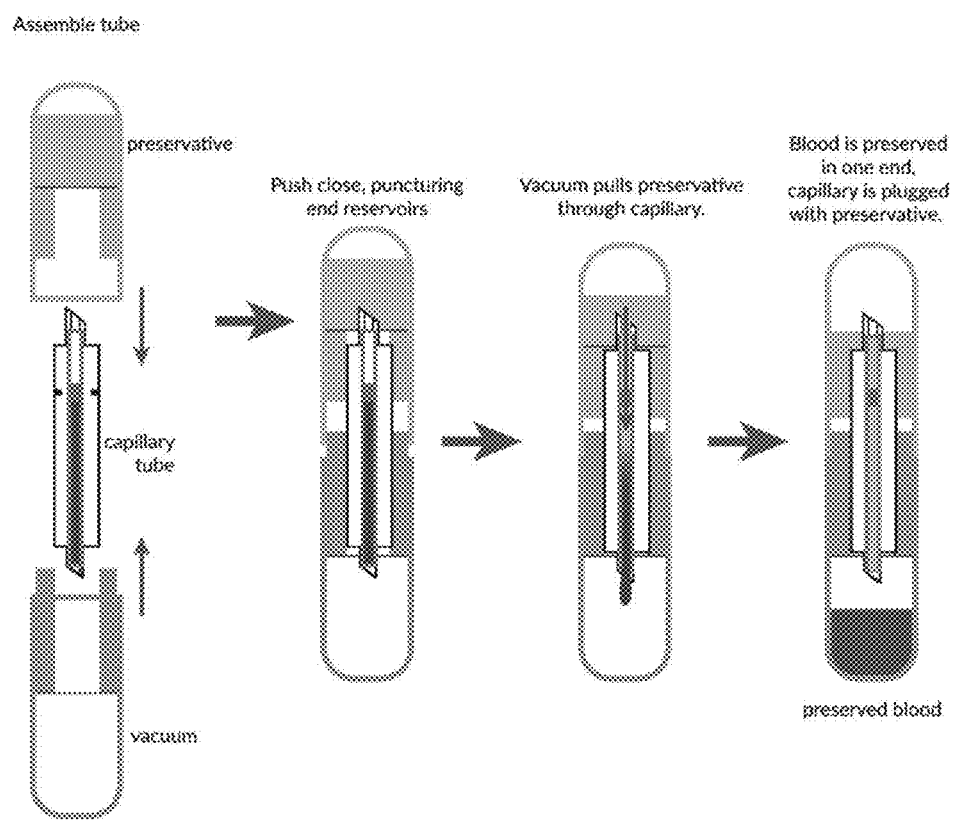
Figure 12C:
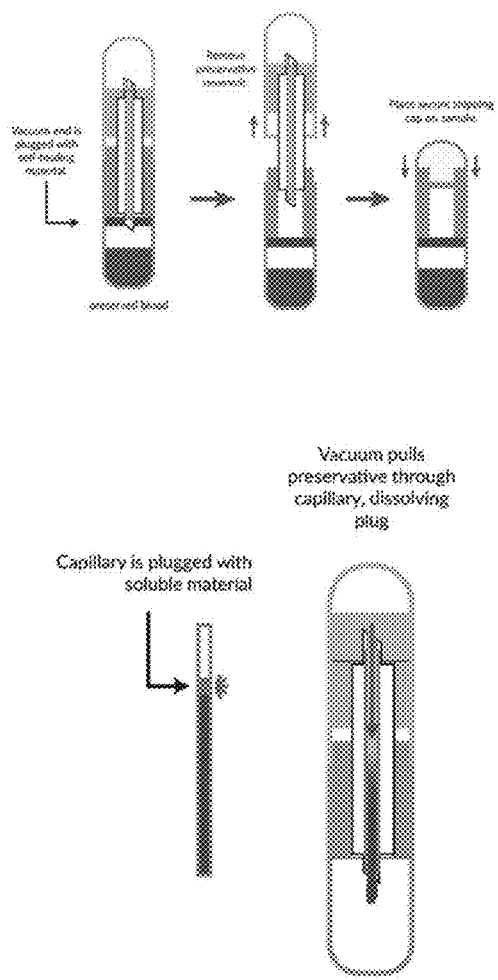

FIG. 12A-12C illustrate examples of a kit for taking blood samples according to some embodiments of the present technology. In some embodiments, porous, soluble plugs help to ensure a steady flow of blood into the capillary. These plugs can also increase pressure within the tube once the blood reaches it, giving an indication to the sampling device that the correct amount of blood has been drawn. Minimizing bubbles/air in the sample tube can be important for proper mobilization readings. So, some embodiments of the present technology involve detecting bubbles and missing blood within the provided sample through imaging of the capillary following the blood draw. For example, a user can place the capillary on a designated background provided in the kit and take an image through the provided software program.

Figure 12D:
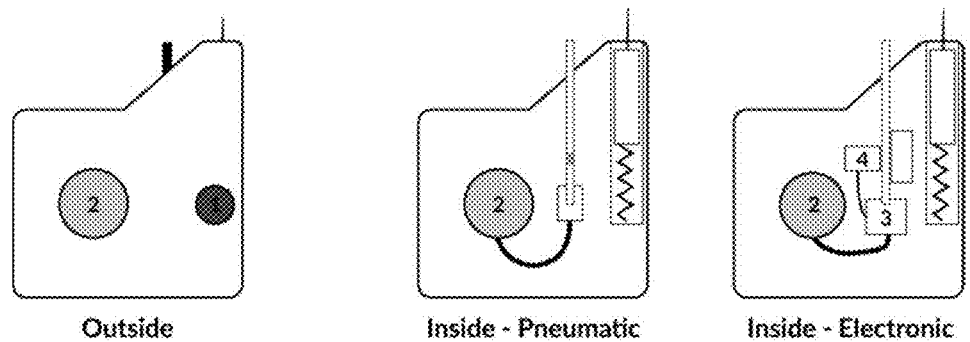

FIG. 12D illustrates a blood drawing device according to some embodiments of the present technology. The blood drawing device can contain a capillary port which houses a capillary with a holding capacity of 20-100 ul of whole blood. The blood drawing device can also involve separate or combined triggers (button 1,2) that can drive the lancet (for opening the skin) and controlled suction for proper sampling of blood. In some cases, a light sensor (3) and/or pressure sensor (4) determines when sufficient blood has been drawn into the capillary and gives a visual and/or auditory cue indicating a successful draw.

Some embodiments of the present technology involve ensuring that the baseline reading captured by the kit is a true baseline. Illness and certain drugs can change the immune system significantly enough to reduce the accuracy of the baseline readings that will be used by the software program. Accordingly, some embodiments of the present technology involve methods to ensure proper baselines are established. For example, ensuring a proper baseline can involve informing the customer how long to wait after being sick and how long to wait after being exposed to anyone who was sick before drawing the blood. Ensuring a proper baseline can also involve measuring common viral Deoxyribonucleic acid (DNA) or ribonucleic acid (RNA), by using polymerase chain reaction (PCR) analysis on submitted samples, measuring T cell markers and relative WBC levels that deviate from the norm, analyzing multiple baseline blood samples provided by the user over the course of several days, and using physiological measurements from the fitness tracker, such as resting heart rate, skin temperature, etc., to identify when the user is in a state outside of a normal healthy baseline.

As described above, one aspect of the present technology is the gathering and use of data available from various sources. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, or any other identifying information.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

Figure 13A:
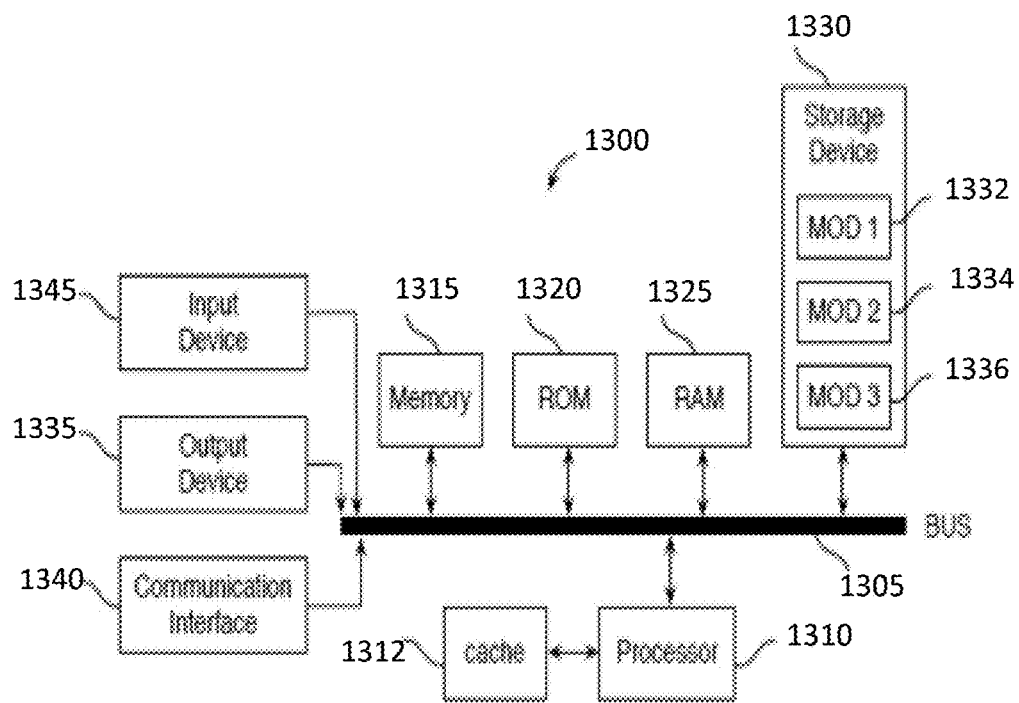
FIG. 13A and FIG. 13B illustrate exemplary possible system embodiments.
Figure 13B:
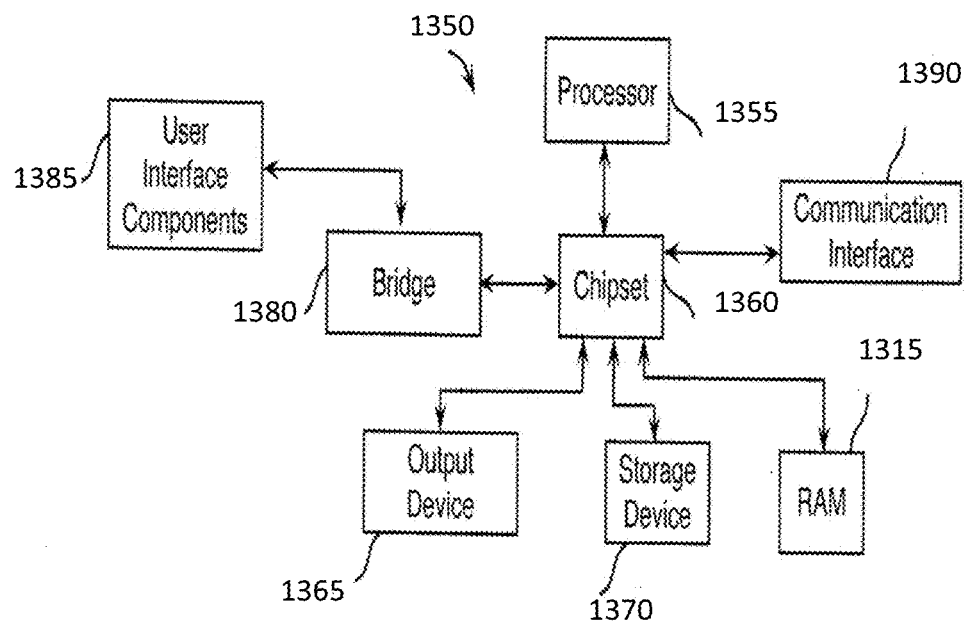

FIG. 13A and FIG. 13B illustrate exemplary possible system embodiments. The more appropriate embodiment will be apparent to those of ordinary skill in the art when practicing the present technology. Persons of ordinary skill in the art will also readily appreciate that other system embodiments are possible.

FIG. 13A illustrates a conventional system bus computing system architecture 1300 wherein the components of the system are in electrical communication with each other using a bus 1305. Exemplary system 1300 includes a processing unit (CPU or processor) 1310 and a system bus 1305 that couples various system components including the system memory 1315, such as read only memory (ROM) 1320 and random access memory (RAM) 1325, to the processor 1310. The system 1300 can include a cache of high-speed memory connected directly with, in close proximity to, or integrated as part of the processor 1310. The system 1300 can copy data from the memory 1315 and/or the storage device 1330 to the cache 1312 for quick access by the processor 1310. In this way, the cache can provide a performance boost that avoids processor 1310 delays while waiting for data. These and other modules can control or be configured to control the processor 1310 to perform various actions. Other system memory 1315 may be available for use as well. The memory 1315 can include multiple different types of memory with different performance characteristics. The processor 1310 can include any general purpose processor and a hardware module or software module, such as module 1 1332, module 2 1334, and module 3 1336 stored in storage device 1330, configured to control the processor 1310 as well as a special-purpose processor where software instructions are incorporated into the actual processor design. The processor 1310 may essentially be a completely self-contained computing system, containing multiple cores or processors, a bus, memory controller, cache, etc. A multi-core processor may be symmetric or asymmetric.

To enable user interaction with the computing device 1300, an input device 1345 can represent any number of input mechanisms, such as a microphone for speech, a touch-sensitive screen for gesture or graphical input, keyboard, mouse, motion input, speech and so forth. An output device 1335 can also be one or more of a number of output mechanisms known to those of skill in the art. In some instances, multimodal systems can enable a user to provide multiple types of input to communicate with the computing device 1300. The communications interface 1340 can generally govern and manage the user input and system output. There is no restriction on operating on any particular hardware arrangement and therefore the basic features here may easily be substituted for improved hardware or firmware arrangements as they are developed.

Storage device 1330 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1325, read only memory (ROM) 1320, and hybrids thereof.

The storage device 1330 can include software modules 1332, 1334, 1336 for controlling the processor 1310. Other hardware or software modules are contemplated. The storage device 1330 can be connected to the system bus 1305. In one aspect, a hardware module that performs a particular function can include the software component stored in a computer-readable medium in connection with the necessary hardware components, such as the processor 1310, bus 1305, display 1335, and so forth, to carry out the function.

FIG. 13B illustrates a computer system 1350 having a chipset architecture that can be used in executing the described method and generating and displaying a graphical user interface (GUI). Computer system 1350 is an example of computer hardware, software, and firmware that can be used to implement the disclosed technology. System 1350 can include a processor 1355, representative of any number of physically and/or logically distinct resources capable of executing software, firmware, and hardware configured to perform identified computations. Processor 1355 can communicate with a chipset 1360 that can control input to and output from processor 1355. In this example, chipset 1360 outputs information to output 1365, such as a display, and can read and write information to storage device 1370, which can include magnetic media, and solid state media, for example. Chipset 1360 can also read data from and write data to RAM 1375. A bridge 1380 for interfacing with a variety of user interface components 1385 can be provided for interfacing with chipset 1360. Such user interface components 1385 can include a keyboard, a microphone, touch detection and processing circuitry, a pointing device, such as a mouse, and so on. In general, inputs to system 1350 can come from any of a variety of sources, machine generated and/or human generated.

Chipset 1360 can also interface with one or more communication interfaces 1390 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1355 analyzing data stored in storage 1370 or 1375. Further, the machine can receive inputs from a user via user interface components 1385 and execute appropriate functions, such as browsing functions by interpreting these inputs using processor 1355.

It can be appreciated that exemplary systems 1300 and 1350 can have more than one processor 1310 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The invention claimed is:

1. An apparatus comprising:
   a display associated with a user input;
   an activity sensor coupled with a processor, a communication interface, and a memory storing instructions that, when executed by the processor, cause the apparatus to:
      receive, through the user input, self-reported user information;
      create, based on the self-reported user information, a recommended baseline activity regimen for achieving at least one immunity-related goal, the at least one immunity-related goal comprising one or more of immune cell or progenitor mobilization, altering circulation rates of one of immune cells or progenitors, changes in absolute or relative abundance of immune cell types in circulation, alterations in one of abundance or localization of immune cell proteins, changes in RNA expression, or alterations of immune cell structure;
      display the recommended baseline activity regimen;
      receive activity data for the user from the activity sensor, the activity data including one or more of heart rate, acceleration, blood pressure, external temperature, body temperature, geographical location, pressure, skin conductance, blood oxygen level, or glucose level;
      determine, by providing the activity data to an immune-response prediction model, when the activity data indicates a user activity that deviates from the recommended baseline activity regimen to a predetermined threshold degree; and
      provide feedback to the user for correcting the deviation from the recommended baseline activity regimen; and
   a blood collection kit containing a blood collection apparatus and a blood preservation and storage unit, the blood collection kit configured to collect a user's blood after performing the recommended baseline activity regimen and send the collected blood sample to a blood analysis entity; wherein the communication interface is further configured to receive, from a network location associated with the blood analysis entity, a set of blood analysis results; and wherein the instructions further cause the apparatus to update the recommended baseline activity regimen using the blood analysis results.

2. The apparatus of claim 1, wherein the instructions further cause the apparatus to:
   receive, from the user through the user input, a user authorization for access to user blood sample data from a network location;
   retrieve, using the communication interface, blood sample data from the network location; and
   update the recommended baseline activity regimen based on the blood sample data.

3. The apparatus of claim 2, wherein the instructions further cause the apparatus to personalize the recommended baseline activity regimen based on the blood sample data to create an updated activity regimen that increases the mobilization of one or more specific blood cells.

4. The apparatus of claim 2, wherein the blood sample data comprises data for multiple blood draws performed over a period of time, and wherein the instructions further cause the apparatus to update the recommended baseline activity regimen based on the blood sample data to create an updated activity regimen that increases a mobilization stacking effect on blood cell mobilization.

5. The apparatus of claim 1, wherein the instructions further cause the apparatus to create a recommended baseline activity regimen for achieving at least one immunity-related goal by inputting the self-reported user information into mobilization prediction model stored in the memory.

6. The apparatus of claim 1, wherein the instructions further cause the communication interface to:
   transmit the self-reported user information to a network location containing a program for creating a recommended baseline activity regimen for achieving at least one immunity-related goal by inputting the self-reported user information into a mobilization prediction model; and
   receive the recommended baseline activity regimen from the network location.

7. The apparatus of claim 1, wherein the instructions further cause the apparatus to display, as part of the recommended baseline activity regimen, one or more of an activity type, an exertion intensity and an exertion duration.

8. The apparatus of claim 1, wherein the activity sensor comprises one or more of a heart rate monitor, an accelerometer, a blood pressure monitor, an external temperature monitor, a body temperature monitor, a location tracking system, a pressure sensor, a skin conductance sensor, and a blood oxygen level sensor.

9. The apparatus of claim 1, wherein the instructions further cause the apparatus to:
   display an interface element that allows a user to request to access, though the communication interface, personal genetic information from a network location; and
   receive, through the communication interface, personal genetic information from a network location;

wherein the self-reported user information includes the personal genetic information including one or more of simple nucleotide polymorphism data and full genetic sequencing data.

* * * * *